United States Patent
Himmelsbach et al.

(10) Patent No.: US 10,730,850 B2
(45) Date of Patent: Aug. 4, 2020

(54) PYRIDINYLMETHYL CARBAMIMIDOYLCARBAMATE DERIVATIVES AND THEIR USE AS AOC3 INHIBITORS

(71) Applicant: Boehringer Ingelheim International GmbH, Ingelheim am Rhein (DE)

(72) Inventors: Frank Himmelsbach, Mittelbiberach (DE); Andreas Blum, Darmstadt (DE); Stefan Peters, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/080,328

(22) PCT Filed: Mar. 3, 2016

(86) PCT No.: PCT/EP2016/054541
§ 371 (c)(1),
(2) Date: Aug. 28, 2018

(87) PCT Pub. No.: WO2017/148519
PCT Pub. Date: Sep. 8, 2017

(65) Prior Publication Data
US 2019/0084959 A1      Mar. 21, 2019

(51) Int. Cl.
| | | |
|---|---|---|
| C07D 401/04 | (2006.01) | |
| C07D 401/14 | (2006.01) | |
| C07D 405/14 | (2006.01) | |
| C07D 401/12 | (2006.01) | |
| C07D 239/42 | (2006.01) | |
| C07D 413/14 | (2006.01) | |
| C07D 213/80 | (2006.01) | |
| C07D 213/85 | (2006.01) | |
| C07D 417/12 | (2006.01) | |
| C07D 213/72 | (2006.01) | |
| C07D 451/02 | (2006.01) | |
| C07D 213/82 | (2006.01) | |
| C07D 487/08 | (2006.01) | |
| C07D 213/84 | (2006.01) | |
| C07D 417/14 | (2006.01) | |
| A61P 1/16 | (2006.01) | |

(52) U.S. Cl.
CPC ............. *C07D 401/04* (2013.01); *A61P 1/16* (2018.01); *C07D 213/72* (2013.01); *C07D 213/80* (2013.01); *C07D 213/82* (2013.01); *C07D 213/84* (2013.01); *C07D 213/85* (2013.01); *C07D 239/42* (2013.01); *C07D 401/12* (2013.01); *C07D 401/14* (2013.01); *C07D 405/14* (2013.01); *C07D 413/14* (2013.01); *C07D 417/12* (2013.01); *C07D 417/14* (2013.01); *C07D 451/02* (2013.01); *C07D 487/08* (2013.01)

(58) Field of Classification Search
CPC .................................. C07D 401/04; A61P 1/18
See application file for complete search history.

(56) References Cited

FOREIGN PATENT DOCUMENTS

| | | | |
|---|---|---|---|
| CA | 2830157 A1 | 9/2012 | |
| EP | 2695881 A1 | 2/2014 | |
| JP | 2008512346 A | 4/2008 | |
| WO | 2006028269 | 3/2006 | |
| WO | WO 2009026319 | * 2/2009 | ........... C07D 239/26 |
| WO | 12120195 A1 | 9/2012 | |
| WO | 12124696 A1 | 9/2012 | |
| WO | 2017148519 A1 | 9/2017 | |

OTHER PUBLICATIONS

Nobili. World Journal of Gastroentrology, 2009, 15(48), 6017-6022 (Year: 2009).*
Shen. UC Berkeley thesis, 2010, 1-145 (Year: 2010).*
International Search Report for PCT/EP2016/054541 dated May 27, 2016.

* cited by examiner

*Primary Examiner* — Noble E Jarrell
(74) *Attorney, Agent, or Firm* — David L. Kershner

(57) ABSTRACT

The invention relates to new heteroaryl derivatives of the formula wherein X is selected from the group consisting of: N and CH; X is selected from the group consisting of: N and CF; (with the proviso that at least one of $X^1$ and $X^2$ is N), and A is as defined in the description and claims, to their use as medicaments, to methods for their therapeutic use and to pharmaceutical compositions containing them.

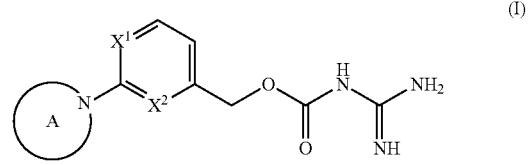

(I)

13 Claims, No Drawings

PYRIDINYLMETHYL CARBAMIMIDOYLCARBAMATE DERIVATIVES AND THEIR USE AS AOC3 INHIBITORS

FIELD OF THE INVENTION

This invention relates to new compounds, in particular heteroaryl derivatives, to processes for preparing such compounds, to their use as inhibitors of AOC3, to methods for their therapeutic use, in particular in diseases and conditions mediated by the inhibition of AOC3, and to pharmaceutical compositions comprising them.

BACKGROUND OF THE INVENTION

The enzymatic activity of AOC3 (amine oxidase, copper containing 3; vascular adhesion protein 1) has been described already in 1967 as a monoamine oxidase activity in the plasma of chronic liver disease patients (Gressner, A. M. et al., 1982, J. Clin. Chem. Clin. Biochem. 20: 509-514; McEwen, C. M., Jr. et al., 1967, J. Lab Clin. Med. 70: 36-47). AOC3 has two closely homologous genes in the human genome: AOC1 which corresponds to a diamine oxidase (Chassande, O. et al., 1994, J. Biol. Chem. 269: 14484-14489) and AOC2, a SSAO with a specific expression in the retina (Imamura, Y. et al., 1997, Genomics 40: 277-283). AOC4 is a sequence that does not lead to a functional gene product in humans due to an internal stop-codon (Schwelberger, H. G., 2007, J. Neural Transm. 114: 757-762).

The enzyme contains an oxidized 2,4,5-trihydroxy-phenalalanyl-quinone (TPQ) and a copper ion in the active side. This characteristic catalytic center classifies the semi-carbazide-sensitive amine oxidase (SSAO, copper-containing amine:oxygen oxido-reductase (deaminating)): The type II membrane protein belongs to the family of copper containing amine oxidases together with several other diamine and the lysyl oxidases. However the later enzymes can be distinguished from AOC3 in their preference for diamines and the low sensitivity towards semicarbazide inhibition (Dunkel, P. et al., 2008, Curr. Med. Chem. 15: 1827-1839). On the other hand monoamine oxidases contain the flavin adenine dinucleotide (FAD) cofactor in their reactive center like the monoamine oxidase A (MAO-A) and MAO-B and follow therefore a completely different reaction scheme.

AOC3 catalyzes a two-step reaction mechanism for the oxidative deamination of primary aliphatic and aromatic amines. In a first reaction the primary amine forms a Schiffbase with the TPQ aldehyde. This covalent bond is hydrolyzed, releasing the aldehyde product and a substituted TPQ residue in the active core. In the presence of oxygen, TPQ is oxidized under the formation of ammonia and peroxide with the help of the copper molecule (Mure, M. et al., 2002, Biochemistry 41: 9269-9278). Several substrates of AOC3 have been described, like the physiological amines methylamine, dopamine, or aminoacetone, whose products of oxidation have been associated to cardiovascular pathologies (Yu, P. H. et al., 1993, Diabetes 42: 594-603). Synthetic amines have been optimized for their turnover by AOC3 like benzylaminde derivates (Yraola, F. et al., 2006, J. Med. Chem. 49: 6197-6208), C-Naphthalen-1-methylamine (Marti, L. et al., 2004, J. Med. Chem. 47: 4865-4874) or luciferin derivates (Valley, M. P. et al., 2006, Anal. Biochem. 359: 238-246). The later substrate can be used for the sensitive detection of AOC3 activity in plasma, tissue or for biochemical characterization of the enzyme.

Under pathophysiological conditions of high AOC3 activity the aldehyde products are highly reactive, leading to advanced glycosylation end products (Mathys, K. C. et al., 2002, Biochem. Biophys. Res. Commun. 297: 863-869) which are regarded as markers and drivers of diabetes associated inflammatory mechanisms.

Further the byproduct hydrogen peroxide is sensed by the tissue as a messenger of inflammation. The intermediate is able to activate endothelium and is fostering the activation of leukocytes.

The binding and modification of Siglec-10 as a membrane bound substrate provides a mechanistic understanding of how the enzymatic reaction could trigger the leukocyte transmigration through activated endothelia. The binding of Siglec-10 to AOC3 was shown in several adhesion assays and led to increased hydrogen peroxide production (Kivi, E. et al., 2009, Blood 114: 5385-5392). Binding of activated leukocytes to the dimeric, extracellular AOC3 via the Siglec-10 generates a transient association to the activated endothelial. Therefore the rolling velocity of leukocytes is reduced, which increases the transmigration of leukocytes into the interstitium of inflamed tissues. Further, a conserved RGD-motif on the surface of AOC3 argues for its adhesive role: The deletion of this sequence reduced leukocyte recruitment (Salmi, M. et al., 2000, Circ. Res. 86: 1245-1251) probably via a lack of integrin β1 binding activity (Aspinall, A. I. et al., 2010, Hepatology 51: 2030-2039).

This finding correlates to the phenotype of AOC3 knock out mice, which exert a reduced leukocyte and lymphocyte transmigration capacity (Stolen, C. M. et al., 2005, Immunity. 22: 105-115) into lymphoid organs and adipose tissue (Bour, S. et al., 2009, Am. J. Pathol. 174: 1075-1083).

AOC3 activity can be found in most tissues and is mainly expressed in endothelial cells, smooth muscle cells and adipocytes (Boomsma, F. et al., 2000, Comp Biochem. Physiol C. Toxicol. Pharmacol. 126: 69-78; O'Sullivan, J. et al., 2004, Neurotoxicology 25: 303-315). In humans, in contrast to mice, AOC3 activity is constitutive in the liver sinusoideal endothelial cells (McNab, G. et al., 1996, Gastroenterology 110: 522-528) and mRNA expression is further upregulated under inflammatory conditions in this tissue (Lalor, P. F. et al., 2002, Immunol. Cell Biol. 80: 52-64); Bonder, C. S. et al., 2005, Immunity. 23: 153-163). AOC3 not only exists as a membrane protein, but can also be found as soluble plasma activity probably due to a metalloprotease mediated shedding process (Abella, A. et al., 2004, Diabetologia 47: 429-438); Boomsma, F. et al., 2005, Diabetologia 48: 1002-1007; Stolen, C. M. et al., 2004, Circ. Res. 95: 50-57)). Elevated levels of soluble AOC3 have been observed in diabetes (Li, H. Y. et al., 2009, Clin. Chim. Acta 404: 149-153), obesity (Meszaros, Z. et al., 1999, Metabolism 48: 113-117; Weiss, H. G. et al., 2003, Metabolism 52: 688-692), congestive heart failure (Boomsma, F. et al., 1997, Cardiovasc. Res. 33: 387-391), end-stage renal disease (Kurkijarvi, R. et al., 2001, Eur. J. Immunol. 31: 2876-2884) and inflammatory liver disease (Kurkijarvi, R. et al., 1998, J. Immunol. 161: 1549-1557). For the later, levels of AOC3 plasma activity have been correlated to liver fibrosis and serve as a predictor in patients with NAFLD (Weston, C. J. et al., 2011, J. Neural Transm. 118: 1055-1064). After transplantation of cirrhotic livers, high AOC3 plasma levels dropped drastically, which argues for the liver as the major source of plasma AOC3 activity under this pathological condition (Boomsma, F. et al., 2003, Biochim. Biophys. Acta 1647: 48-54).

The role of AOC3 in the activation of inflammation via peroxide generation and the recruitment of leukocytes to activated endothelium makes it an attractive target for the treatment of inflammatory components in several diseases. Therefore a variety of small molecular compounds and antibodies have been tested in different disease animal models. Amongst those, the inhibition of AOC3 showed beneficial effects in the models of melanoma and lymphoma cancer (Marttila-Ichihara, F. et al., 2010, J. Immunol. 184: 3164-3173), acute and chronic joint (Tabi, T. et al., 2013, J. Neural Transm. 120: 963-967) or lung (Foot, J. S. et al., 2013, J. Pharmacol. Exp. Ther. 347: 365-374) inflammation, diabetic macular edema (Inoue, T. et al., 2013, Bioorg. Med. Chem. 21: 1219-1233), kidney fibrosis (Wong, M. et al., 2014, Am. J. Physiol Renal Physiol 307: F908-F916), liver allograft rejection (Martelius, T. et al., 2004, Am. J. Pathol. 165: 1993-2001) and non-alcoholic liver disease.

The development of a selective, potent and well tolerated AOC3 inhibitor would therefore be beneficial for the treatment of the respective human diseases.

AOC3 inhibitors are known in the art, for example, the compounds disclosed in EP 2 695 881 corresponding to WO 2012/124696. The heteroaryl derivatives of the present invention may provide several advantages, such as enhanced potency, reduced plasma protein binding, improved CYP (cytochrome P450) enzyme profile and high metabolic stability, high chemical stability, improved tissue distribution, improved side effect profile and/or tolerability and in consequence low toxicity, reduced risk to cause adverse events or undesirable side effects, and enhanced solubility. The heteroaryl derivatives of the present invention exhibit increased metabolic stability, enabling less frequent dosing and lower doses as compared to the corresponding phenyl analogues. Moreover, the heteroaryl derivatives of the present invention show reduced biliary clearance, which is expected to be impaired in patients with liver diseases (Clarke J. D. et. al J. Pharm. Exp. Ther. 348:452-458; Ferslew B. C. et al. Clin. Pharm. & Ther. Vol 97(4) XX), resulting in a better predictibitlity of the pharmacokinetics and assessment of safety margins in this patient population.

Aim of the Present Invention

The aim of the present invention is to provide new compounds, in particular new heteroaryl derivatives, which are active with regard to AOC3.

Another aim of the present invention is to provide new compounds, in particular new heteroaryl derivatives, which are active with regard to AOC3.

A further aim of the present invention is to provide new compounds, in particular new heteroaryl derivatives, which have an inhibitory effect on AOC3 in vitro and/or in vivo and possess suitable pharmacological and pharmacokinetic properties to use them as medicaments.

A further aim of the present invention is to provide new compounds, in particular new heteroaryl derivatives, which have an inhibitory effect on AOC3 in vitro and/or in vivo and possess suitable pharmacological and pharmacokinetic properties to use them as medicaments.

A further aim of the present invention is to provide effective AOC3 inhibitors, in particular for the treatment of various diseases, for example of NASH (non-alcoholic steatohepatitis), retinopathy and nephropathy.

Another aim of the present invention is to provide effective AOC3 inhibitors for the treatment of metabolic disorders such as NASH (non-alcoholic steatohepatitis), retinopathy and nephropathy.

A further aim of the present invention is to provide methods for treating a disease or condition mediated by the inhibition of AOC3 in a patient.

A further aim of the present invention is to provide a pharmaceutical composition comprising at least one compound according to the invention.

A further aim of the present invention is to provide a combination of at least one compound according to the invention with one or more additional therapeutic agents.

A further aim of the present invention is to provide methods for the synthesis of the new compounds, in particular heteroaryl derivatives.

A further aim of the present invention is to provide starting and/or intermediate compounds suitable in methods for the synthesis of the new compounds.

Further aims of the present invention become apparent to the one skilled in the art by the description hereinbefore and in the following and by the examples.

Object of the Invention

Within the scope of the present invention it has now surprisingly been found that the new compounds of general formula (I) as described hereinafter exhibit an inhibiting activity with regard to AOC3.

According to another aspect of the present invention it has been found that the new compounds of general formula (I) as described hereinafter exhibit an inhibiting activity with regard to AOC3.

In a first aspect the present invention provides a compound of general formula

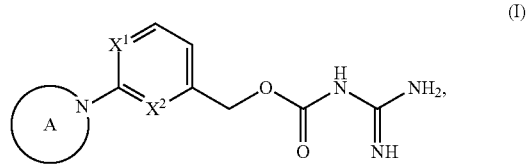

wherein $X^1$ is selected from the group $X^1$-G1 consisting of: N and CH;

$X^2$ is selected from the group $X^2$-G1 consisting of: N and CF;

whith the proviso that at least one of $X^1$ and $X^2$ is N;

A is selected from the group A-G1 consisting of:

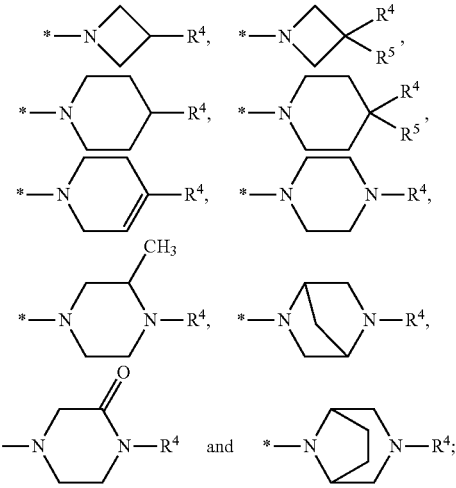

$R^4$ is selected from the group $R^4$-G1 consisting of: azetidinyl, pyrrolidinyl, piperidinyl, piperazinyl, morpholinyl, tetrahydropyranyl, oxazolidinyl, $C_{3-8}$-cycloalkyl, phenyl, pyridinyl, pyrazinyl, pyridazinyl, pyrimidinyl, [1,3,5]triazinyl, triazolyl, thiazolyl, imidazo[1,2-a]pyridin-2-yl, 2,3-dihydro-1H-isoindolyl, oxazolyl and oxadiazolyl, wherein each $R^4$ is optionally substituted with one or more groups independently of each other selected from a group consisting of halogen, OH, $CO_2H$, CN, $CF_3$, $C_{1-3}$-alkyl, $C_{3-6}$-cycloalkyl, $C_{1-3}$-alkyl-O—, $(R^N)_2N$—, $C_{1-3}$-alkyl-C(=O)—, $C_{1-4}$-alkyl-O—C(=O)—, $(R^N)_2N$—C(=O)—, $(R^N)_2N$—$C_{1-3}$-alkyl-, $C_{3-6}$-cycloalkyl-$C_{1-3}$-alkyl-O—, $C_{1-3}$-alkyl-$SO_2$—, $(R^N)_2N$—$SO_2$—, 2-oxo-pyrrolidinyl and $C_{1-3}$-alkyl-C(=O)—$(R^N)N$—$C_{1-3}$-alkyl-; and wherein a —$CH_2$-group of the pyrrolidinyl, 2,3-dihydro-1H-isoindolyl, oxazolidinyl, piperidinyl or piperazinyl group of $R^4$ is optionally replaced with a —C(=O)—, —S(=O)— or —$S(=O)_2$— group;

$R^N$ is selected from the group $R^4$-G1 consisting of: H and $C_{1-4}$-alkyl, wherein, if several $R^N$ groups are present, they may be indentical or different from one another;

$R^5$ is selected from the group $R^5$-G1 consisting of: CN and OH; or, $R^4$ and $R^5$ groups together with the carbon atom, to which they are attached, may form the following group:

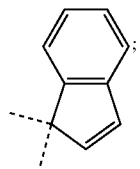

wherein each of the above-mentioned alkyl and —O-alkyl groups may be linear or branched and are optionally substituted by one or more F;

a tautomer or stereoisomers thereof,
or a salt thereof,
or a solvate or hydrate thereof.

In a further aspect the present invention relates to processes for preparing a compound of general formula (I) and to new intermediate compounds in these processes.

A further aspect of the invention relates to a salt of the compounds of general formula (I) according to this invention, in particular to a pharmaceutically acceptable salt thereof.

In a further aspect this invention relates to a pharmaceutical composition, comprising one or more compounds of general formula (I) or one or more pharmaceutically acceptable salts thereof according to the invention, optionally together with one or more inert carriers and/or diluents.

In a further aspect this invention relates to a method for treating diseases or conditions which are mediated by inhibiting the activity of AOC3 in a patient in need thereof characterized in that a compound of general formula (I) or a pharmaceutically acceptable salt thereof is administered to the patient.

According to another aspect of the invention, there is provided a method for treating NASH (non-alcoholic steatohepatitis), retinopathy or nephropathy in a patient in need thereof characterized in that a compound of general formula (I) or a pharmaceutically acceptable salt thereof is administered to the patient.

According to another aspect of the invention, there is provided the use of a compound of the general formula (I) or a pharmaceutically acceptable salt thereof for the manufacture of a medicament for a therapeutic method as described above or hereinafter.

According to another aspect of the invention, there is provided a compound of the general formula (I) or a pharmaceutically acceptable salt thereof for use in a therapeutic method as described above or hereinafter.

In a further aspect this invention relates to a method for treating a disease or condition mediated by the inhibition of AOC3 in a patient that includes the step of administering to the patient in need of such treatment a therapeutically effective amount of a compound of the general formula (I) or a pharmaceutically acceptable salt thereof in combination with a therapeutically effective amount of one or more additional therapeutic agents.

In a further aspect this invention relates to a use of a compound of the general formula (I) or a pharmaceutically acceptable salt thereof in combination with one or more additional therapeutic agents for the treatment or prevention of diseases or conditions which are mediated by the inhibition of AOC3.

In a further aspect this invention relates to a pharmaceutical composition which comprises a compound according to general formula (I) or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly A, $X^1$, $X^2$, $R^4$, $R^5$ and $R^N$, are defined as above and hereinafter. If residues, substituents or groups occur several times in a compound, as for example $R^N$, they may have the same or different meanings. Some preferred meanings of individual groups and substituents of the compounds according to the invention will be given hereinafter. Any and each of these definitions may be combined with each other.

$X^1$, $X^2$:

The groups $X^1$ and $X^2$ are preferably selected from the groups $X^1$-G1 and $X^2$-G1, resp., as defined above, provided that at least one of $X^1$ and $X^2$ is N.

According to one embodiment, $X^1$ is N and $X^2$ is N or CF.

According to a second embodiment, $X^1$ is N and $X^2$ is CF.

According to a third embodiment, $X^1$ is N or CH and $X^2$ is N.

According to a fourth embodiment, $X^1$ is CH and $X^2$ is N.

According to fifth embodiment, $X^1$ is N and $X^2$ is N.

A:

A-G1:

The group A is preferably selected from the group A-G1 as defined above.

A-G2:

In another embodiment the group A is selected from the group A-G2 consisting of:

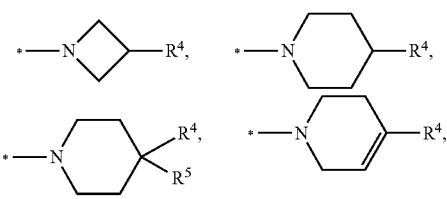

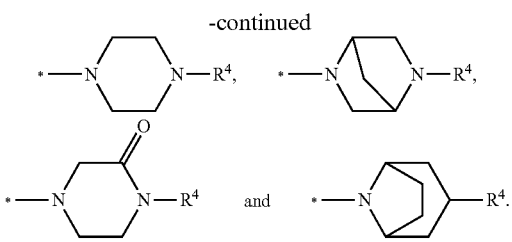

A-G3:

In another embodiment the group A is selected from the group A-G3 consisting of:

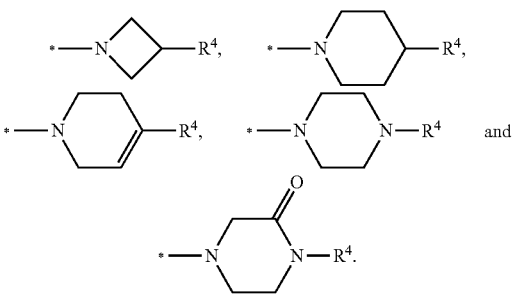

A-G4:

In another embodiment the group A is selected from the group A-G4 consisting of:

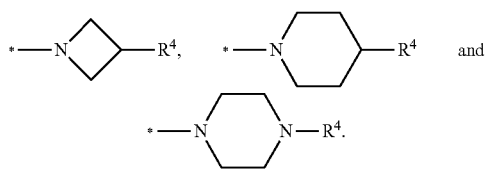

A-G5:

In another embodiment the group A is selected from the group A-G5 consisting of:

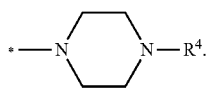

$R^4$:

$R^4$-G1:

The group $R^4$ is preferably selected from the group $R^4$-G1 as defined above.

$R^4$-G2:

In one embodiment the group $R^4$ is selected from the group $R^4$-G2 consisting of: azetidinyl, piperidinyl, piperazinyl, morpholinyl, tetrahydropyranyl, oxazolidinyl, $C_{3-8}$-cycloalkyl, phenyl, pyridinyl, pyridazinyl, pyrimidinyl, [1,3,5]triazinyl, thiazolyl, 2,3-dihydro-1H-isoindolyl and oxazolyl, wherein each $R^4$ is optionally substituted with one or more groups independently of each other selected from a group consisting of halogen, $CO_2H$, CN, $CF_3$, $C_{1-3}$-alkyl, $C_{3-6}$-cycloalkyl, $C_{1-3}$-alkyl-O—, $C_{1-3}$-alkyl-C(=O)—, $C_{1-4}$-alkyl-O—C(=O)—, $(R^N)_2N$—C(=O)—, $(R^N)_2N$—$C_{1-3}$-alkyl-, $C_{3-6}$-cycloalkyl-$C_{1-3}$-alkyl-O—, $C_{1-3}$-alkyl-$SO_2$—, $(R^N)_2N$—$SO_2$— and 2-oxo-pyrrolidinyl; and wherein a —$CH_2$— group of the 2,3-dihydro-1H-isoindolyl, oxazolidinyl, piperidinyl or piperazinyl group of $R^4$ is optionally replaced with a —C(=O)—, —S(=O)— or —S(=O)$_2$— group.

$R^4$-G2a:

In one embodiment the group $R^4$ is selected from the group $R^4$-G2a consisting of: azetidinyl, piperidinyl, piperazinyl, morpholinyl, tetrahydropyranyl, oxazolidinyl, $C_{5-6}$-cycloalkyl, phenyl, pyridinyl, pyridazinyl, pyrimidinyl, [1,3,5]triazinyl, thiazolyl, 2,3-dihydro-1H-isoindolyl and oxazolyl, wherein each $R^4$ is optionally substituted with one or two groups independently of each other selected from thae group consisting of F, Cl, $CO_2H$, CN, $CF_3$, $C_{1-3}$-alkyl, cyclopentyl, $C_{1-3}$-alkyl-O—, $CH_3$—C(=O)—, $C_{1-4}$-alkyl-O—C(=O)—, $(R^N)_2N$—C(=O)—, $(R^N)_2N$—$C_{1-3}$-alkyl-, cyclopropyl-$CH_2$-alkyl-O—, $CH_3$—$SO_2$—, $H_2N$—$SO_2$— and 2-oxo-pyrrolidinyl; and wherein a —$CH_2$— group of the 2,3-dihydro-1H-isoindolyl, oxazolidinyl, piperidinyl or piperazinyl group of $R^4$ is optionally replaced with a —C(=O)— or —S(=O)— group.

$R^4$-G3:

In one embodiment the group $R^4$ is selected from the group $R^4$-G3 consisting of: piperidinyl, tetrahydropyranyl, phenyl, pyridinyl, pyrimidinyl and 2,3-dihydro-1H-isoindolyl, wherein each $R^4$ is optionally substituted with one or more groups independently of each other selected from a group consisting of halogen, CN, $C_{1-3}$-alkyl, $C_{1-3}$-alkyl-O—, $C_{1-3}$-alkyl-C(=O)—, $C_{1-4}$-alkyl-O—C(=O)—, $(R^N)_2N$—C(=O)—, $C_{1-3}$-alkyl-$SO_2$— and $(R^N)_2N$—$SO_2$—; and wherein a —$CH_2$-group of the 2,3-dihydro-1H-isoindolyl of $R^4$ is optionally replaced with a —C(=O)— group.

$R^4$-G3a:

In one embodiment the group $R^4$ is selected from the group $R^4$-G3a consisting of: piperidinyl, tetrahydropyranyl, phenyl, pyridinyl, pyrimidinyl and 2,3-dihydro-1H-isoindolin-yl, wherein each $R^4$ is optionally substituted with one or two groups independently of each other selected from a group consisting of F, Cl, CN, $CH_3$, $CH_3$—O—, $CH_3$—C(=O)—, $CH_3$—O—C(=O)—, $(R^N)_2N$—C(=O)—, $CH_3$—$SO_2$— and $(R^N)_2N$—$SO_2$.

$R^4$-G4:

In another embodiment the group $R^4$ is selected from the group $R^4$-G4 consisting of: phenyl, pyridinyl and pyrimidinyl, wherein each $R^4$ is optionally substituted with one or two groups independently of each other selected from the group consisting of F, CN, $CH_3$, $CH_3$—O— and $CH_3$—$SO_2$—.

$R^4$-G5:

In another embodiment the group $R^4$ is selected from the group $R^4$-G5 consisting of:

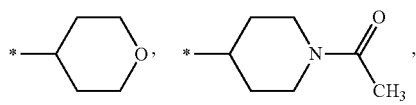

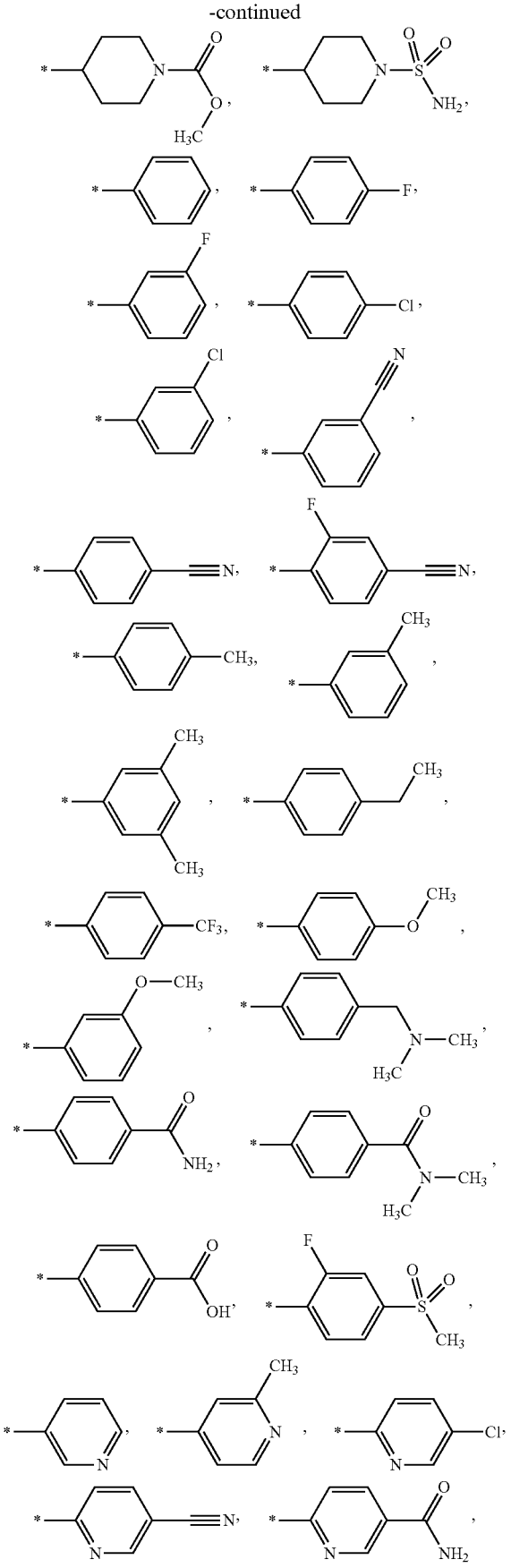
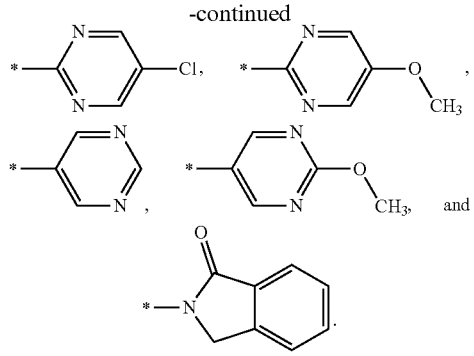

In another embodiment the group $R^4$ is selected from the group $R^4$-G6 consisting of:

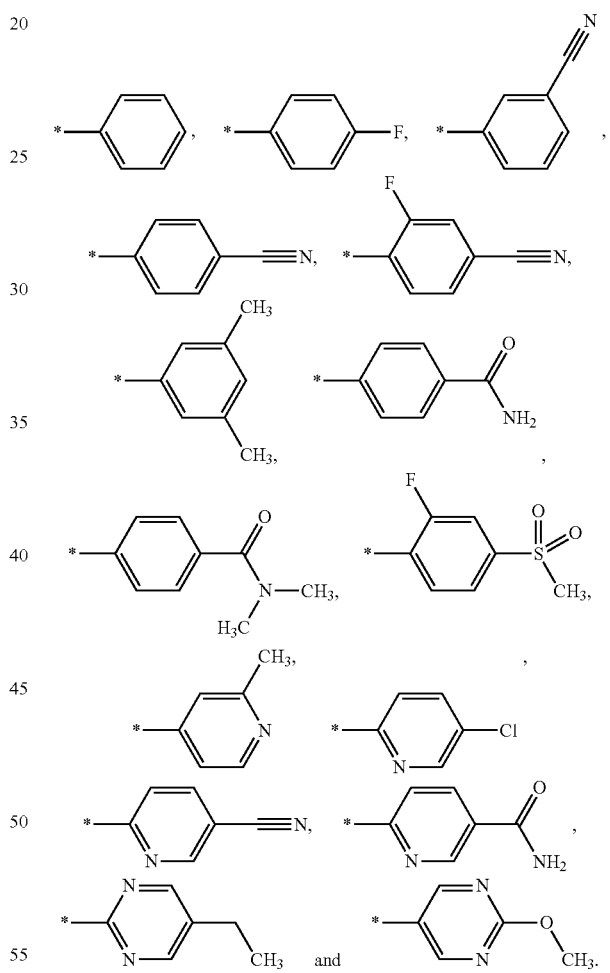

$R^N$:
$R^N$-G1:
The group $R^N$ is preferably selected from the group $R^N$-G1 as defined above.
$R^N$-G2:
In one embodiment the group $R^N$ is selected from the group $R^N$-G2 consisting of of H and $C_{1-2}$-alkyl.
$R^N$-G3:
In another embodiment the group $R^N$ is selected from the group $R^N$-G3 consisting of H and $CH_3$.

$R^N$-G4:

In another embodiment the group $R^N$ is selected from the group $R^N$-G4 consisting of H.

$R^5$:

$R^5$-G1:

The group $R^5$ is preferably selected from the group $R^5$-G1 as defined above.

$R^5$-G2:

In one embodiment the group $R^5$ is selected from the group $R^5$-G2 consisting of: CN.

Examples of preferred subgeneric embodiments according to the present invention are set forth in the following table, wherein each substituent group of each embodiment is defined according to the definitions set forth above and wherein all other substituents of the formula (I) are defined according to the definitions set forth above:

| No. | $X^1$, $X^2$ | A | $R^4$ | $R^5$ | $R^N$ |
|---|---|---|---|---|---|
| 1 | $X^1$ = N and $X^2$ = CF, or $X^1$ = CH and $X^2$ = N, or $X^1$ = N and $X^2$ = N | A-G1 | $R^4$-G1 | $R^5$-G1 | $R^N$-G1 |
| 2 | $X^1$ = N and $X^2$ = CF, or $X^1$ = CH and $X^2$ = N, or $X^1$ = N and $X^2$ = N | A-G2 | $R^4$-G1 | $R^5$-G2 | $R^N$-G1 |
| 3 | $X^1$ = N and $X^2$ = CF, or $X^1$ = CH and $X^2$ = N, or $X^1$ = N and $X^2$ = N | A-G2 | $R^4$-G2 | $R^5$-G2 | $R^N$-G1 |
| 4 | $X^1$ = N and $X^2$ = CF, or $X^1$ = CH and $X^2$ = N, or $X^1$ = N and $X^2$ = N | A-G3 | $R^4$-G1 | — | $R^N$-G2 |
| 5 | $X^1$ = N and $X^2$ = CF, or $X^1$ = CH and $X^2$ = N, or $X^1$ = N and $X^2$ = N | A-G3 | $R^4$-G1 | — | $R^N$-G3 |
| 6 | $X^1$ = N and $X^2$ = CF, or $X^1$ = CH and $X^2$ = N, or $X^1$ = N and $X^2$ = N | A-G3 | $R^4$-G2 | — | $R^N$-G2 |
| 7 | $X^1$ = N and $X^2$ = CF, or $X^1$ = CH and $X^2$ = N, or $X^1$ = N and $X^2$ = N | A-G3 | $R^4$-G2 | — | $R^N$-G3 |
| 8 | $X^1$ = N and $X^2$ = CF, or $X^1$ = CH and $X^2$ = N, or $X^1$ = N and $X^2$ = N | A-G3 | $R^4$-G2a | — | $R^N$-G3 |
| 9 | $X^1$ = N and $X^2$ = CF, or $X^1$ = CH and $X^2$ = N, or $X^1$ = N and $X^2$ = N | A-G3 | $R^4$-G3 | — | $R^N$-G3 |
| 10 | $X^1$ = N and $X^2$ = CF, or $X^1$ = CH and $X^2$ = N, or $X^1$ = N and $X^2$ = N | A-G3 | $R^4$-G3a | — | $R^N$-G3 |
| 11 | $X^1$ = N and $X^2$ = CF, or $X^1$ = CH and $X^2$ = N, or $X^1$ = N and $X^2$ = N | A-G3 | $R^4$-G4 | — | $R^N$-G3 |
| 12 | $X^1$ = N and $X^2$ = CF, or $X^1$ = CH and $X^2$ = N, or $X^1$ = N and $X^2$ = N | A-G3 | $R^4$-G5 | — | $R^N$-G3 |
| 13 | $X^1$ = N and $X^2$ = CF, or $X^1$ = CH and $X^2$ = N, or $X^1$ = N and $X^2$ = N | A-G4 | $R^4$-G1 | — | $R^N$-G2 |
| 14 | $X^1$ = N and $X^2$ = CF, or $X^1$ = CH and $X^2$ = N, or $X^1$ = N and $X^2$ = N | A-G4 | $R^4$-G1 | — | $R^N$-G3 |
| 15 | $X^1$ = N and $X^2$ = CF, or $X^1$ = CH and $X^2$ = N, or $X^1$ = N and $X^2$ = N | A-G4 | $R^4$-G2 | — | $R^N$-G2 |
| 16 | $X^1$ = N and $X^2$ = CF, or $X^1$ = CH and $X^2$ = N, or $X^1$ = N and $X^2$ = N | A-G4 | $R^4$-G2 | — | $R^N$-G3 |
| 17 | $X^1$ = N and $X^2$ = CF, or $X^1$ = CH and $X^2$ = N, or $X^1$ = N and $X^2$ = N | A-G4 | $R^4$-G2a | — | $R^N$-G3 |
| 18 | $X^1$ = N and $X^2$ = CF, or $X^1$ = CH and $X^2$ = N, or $X^1$ = N and $X^2$ = N | A-G4 | $R^4$-G3 | — | $R^N$-G3 |
| 19 | $X^1$ = N and $X^2$ = CF, or $X^1$ = CH and $X^2$ = N, or $X^1$ = N and $X^2$ = N | A-G4 | $R^4$-G3a | — | $R^N$-G3 |
| 20 | $X^1$ = N and $X^2$ = CF, or $X^1$ = CH and $X^2$ = N, or $X^1$ = N and $X^2$ = N | A-G4 | $R^4$-G4 | — | $R^N$-G3 |
| 21 | $X^1$ = N and $X^2$ = CF, or $X^1$ = CH and $X^2$ = N, or $X^1$ = N and $X^2$ = N | A-G4 | $R^4$-G5 | — | $R^N$-G3 |
| 22 | $X^1$ = N and $X^2$ = CF, or $X^1$ = CH and $X^2$ = N, or $X^1$ = N and $X^2$ = N | A-G4 | $R^4$-G6 | — | $R^N$-G3 |
| 23 | $X^1$ = N and $X^2$ = CF, or $X^1$ = CH and $X^2$ = N, or $X^1$ = N and $X^2$ = N | A-G5 | $R^4$-G1 | — | $R^N$-G2 |
| 24 | $X^1$ = N and $X^2$ = CF, or $X^1$ = CH and $X^2$ = N, or $X^1$ = N and $X^2$ = N | A-G5 | $R^4$-G1 | — | $R^N$-G3 |
| 25 | $X^1$ = N and $X^2$ = CF, or $X^1$ = CH and $X^2$ = N, or $X^1$ = N and $X^2$ = N | A-G5 | $R^4$-G2 | — | $R^N$-G2 |
| 26 | $X^1$ = N and $X^2$ = CF, or $X^1$ = CH and $X^2$ = N, or $X^1$ = N and $X^2$ = N | A-G5 | $R^4$-G2 | — | $R^N$-G3 |
| 27 | $X^1$ = N and $X^2$ = CF, or $X^1$ = CH and $X^2$ = N, or $X^1$ = N and $X^2$ = N | A-G5 | $R^4$-G2a | — | $R^N$-G3 |
| 28 | $X^1$ = N and $X^2$ = CF, or $X^1$ = CH and $X^2$ = N, or $X^1$ = N and $X^2$ = N | A-G5 | $R^4$-G3 | — | $R^N$-G3 |
| 29 | $X^1$ = N and $X^2$ = CF, or $X^1$ = CH and $X^2$ = N, or $X^1$ = N and $X^2$ = N | A-G5 | $R^4$-G3a | — | $R^N$-G3 |
| 30 | $X^1$ = N and $X^2$ = CF, or $X^1$ = CH and $X^2$ = N, or $X^1$ = N and $X^2$ = N | A-G5 | $R^4$-G4 | — | $R^N$-G3 |
| 31 | $X^1$ = N and $X^2$ = CF, or $X^1$ = CH and $X^2$ = N, or $X^1$ = N and $X^2$ = N | A-G5 | $R^4$-G5 | — | $R^N$-G3 |
| 34 | $X^1$ = N and $X^2$ = CF, or $X^1$ = CH and $X^2$ = N, or $X^1$ = N and $X^2$ = N | A-G5 | $R^4$-G6 | — | $R^N$-G3 |
| 35 | $X^1$ = N and $X^2$ = CF | A-G1 | $R^4$-G1 | $R^5$-G2 | $R^N$-G1 |
| 36 | $X^1$ = N and $X^2$ = CF | A-G2 | $R^4$-G2 | $R^5$-G2 | $R^N$-G1 |
| 37 | $X^1$ = N and $X^2$ = CF | A-G3 | $R^4$-G1 | — | $R^N$-G1 |
| 38 | $X^1$ = N and $X^2$ = CF | A-G3 | $R^4$-G2 | — | $R^N$-G2 |
| 39 | $X^1$ = N and $X^2$ = CF | A-G3 | $R^4$-G2a | — | $R^N$-G2 |
| 40 | $X^1$ = N and $X^2$ = CF | A-G3 | $R^4$-G3 | — | $R^N$-G3 |
| 41 | X1 = N and X2 = CF | A-G3 | $R^4$-G4 | — | $R^N$-G3 |
| 42 | X1 = N and X2 = CF | A-G4 | $R^4$-G1 | — | $R^N$-G2 |
| 43 | X1 = N and X2 = CF | A-G4 | $R^4$-G2 | — | $R^N$-G2 |
| 44 | X1 = N and X2 = CF | A-G4 | $R^4$-G2a | — | $R^N$-G2 |
| 45 | X1 = N and X2 = CF | A-G4 | $R^4$-G3 | — | $R^N$-G3 |
| 46 | X1 = N and X2 = CF | A-G4 | $R^4$-G4 | — | $R^N$-G3 |
| 47 | X1 = N and X2 = CF | A-G5 | $R^4$-G3a | — | $R^N$-G3 |

The following preferred embodiments of compounds of the formula (I) are described using generic formulae (I.1) to (I.3), wherein any tautomers and stereoisomers, solvates, hydrates and salts thereof, in particular the pharmaceutically acceptable salts thereof, are encompassed.

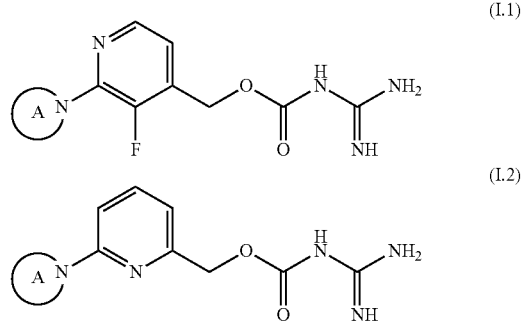

-continued

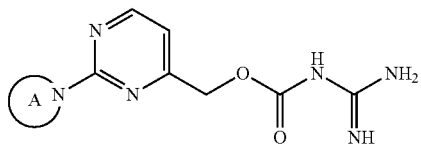
(I.3)

wherein in of the above formulae (I.1) to (I.3), the group A is as defined above.

A preferred embodiment of the present invention concerns compounds of formula

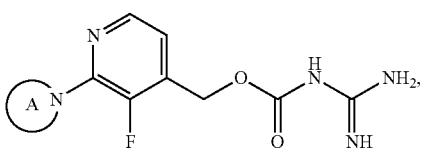
(I.1)

wherein
A is selected from a group consisting of:

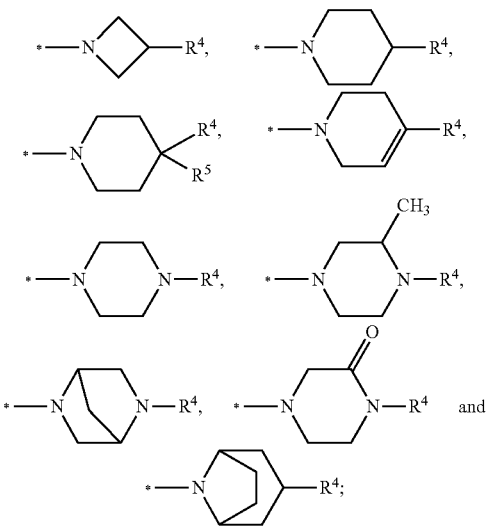

R⁴ is selected from a group consisting of: azetidinyl, piperidinyl, piperazinyl, morpholinyl, tetrahydropyranyl, oxazolidinyl, $C_{3-8}$-cycloalkyl, phenyl, pyridinyl, pyridazinyl, pyrimidinyl, [1,3,5]triazinyl, thiazolyl, 2,3-dihydro-1H-isoindolyl and oxazolyl,
  wherein each R⁴ is optionally substituted with one or more groups independently of each other selected from a group consisting of halogen, $CO_2H$, CN, $CF_3$, $C_{1-3}$-alkyl, $C_{3-6}$-cycloalkyl, $C_{1-3}$-alkyl-O—, $C_{1-3}$-alkyl-C(=O)—, $C_{1-4}$-alkyl-O—C(=O)—, $(R^N)_2N$—C(=O)—, $(R^N)_2N$—$C_{1-3}$-alkyl-, $C_{3-6}$-cycloalkyl-$C_{1-3}$-alkyl-O—, $C_{1-3}$-alkyl-$SO_2$—, $(R^N)_2N$—$SO_2$— and 2-oxo-pyrrolidinyl; and
  wherein a —$CH_2$— group of the 2,3-dihydro-1H-isoindolyl, oxazolidinyl, piperidinyl or piperazinyl group of R⁴ is optionally replaced with a —C(=O)— or —S(=O)— group;
$R^N$ is H or $CH_3$, wherein, if several $R^N$ groups are present, they may be indentical or different from one another;

R⁵ is CN;
or, R⁴ and R⁵ groups together with the carbon atom, to which they are attached, may form the following group:

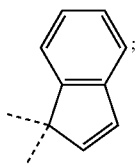
;

wherein each of the above-mentioned alkyl and —O-alkyl groups may be linear or branched and are optionally substituted by one or more F;
or a pharmaceutically acceptable salt thereof.

Another preferred embodiment of the present invention concerns compounds of formula (I), wherein
$X^1$ is N and $X^2$ is CF, or
$X^1$ is CH and $X^2$ is N, or
$X^1$ is N and $X^2$ is N;
A is

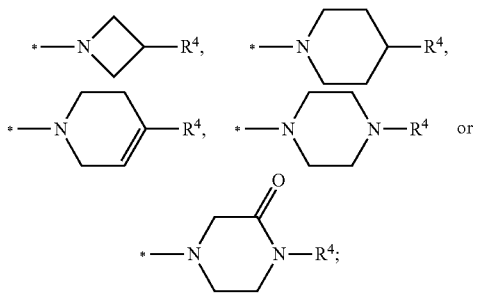

and
R⁴ is selected from a group consisting of piperidinyl, tetrahydropyranyl, phenyl, pyridinyl, pyrimidinyl and 2,3-dihydro-1H-isoindolyl,
  wherein each R⁴ is optionally substituted with one substitutent selected from a group consisting of F, Cl, CN, $CH_3$, $CF_3$, —$CH_2CH_3$, —O—$CH_3$, —$CH_2$—$N(CH_3)_2$, —$CO_2H$, —(C=O)—O—$CH_3$, —C(=O)—$CH_3$, —C(=O)—$NH_2$, —C(=O)—$N(CH_3)_2$, —$SO_2$—$NH_2$ and —$SO_2$—$CH_3$;
  or wherein R⁴ may be substituted with two substitutents, which are independently of each other selected from a group consisting of F, CN and $CH_3$;
or a pharmaceutically acceptable salt thereof.

Preferred compounds of the invention include:

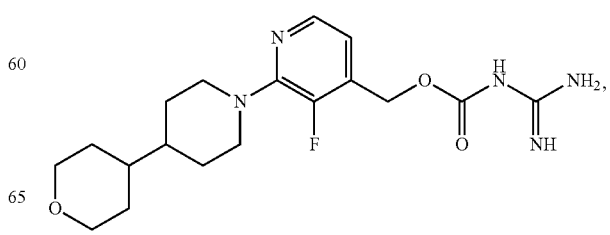

-continued
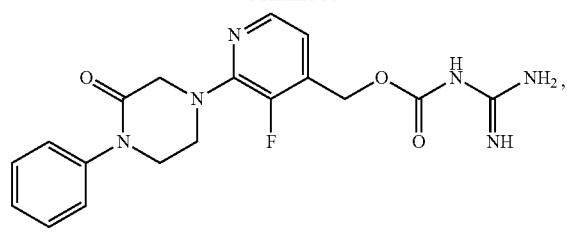
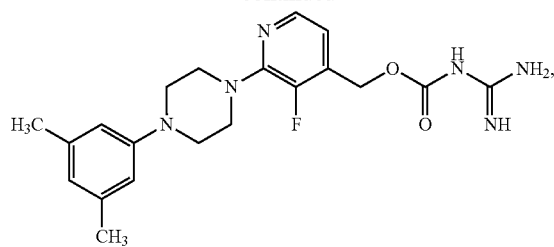
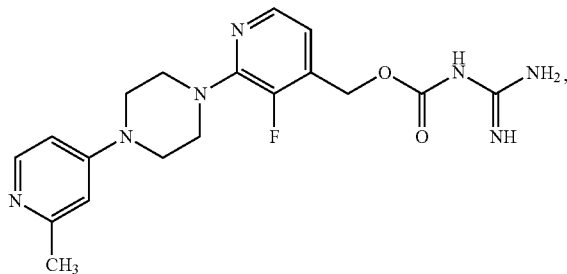
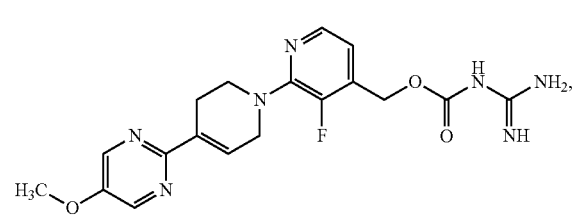
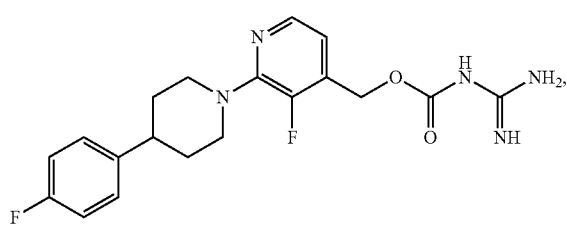
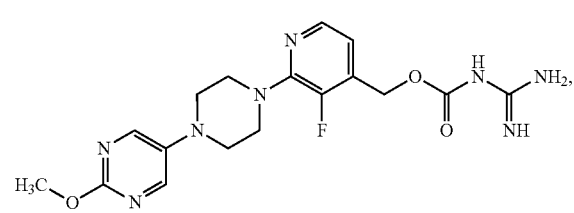
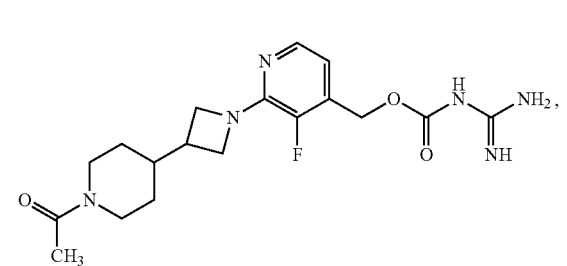
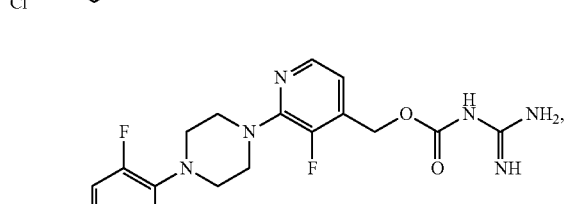
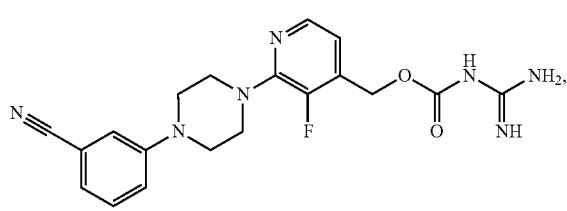
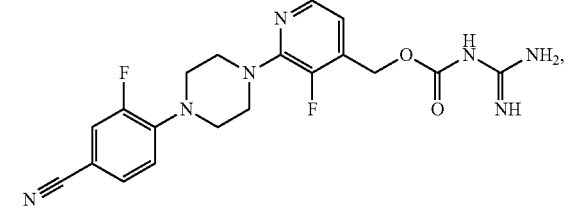
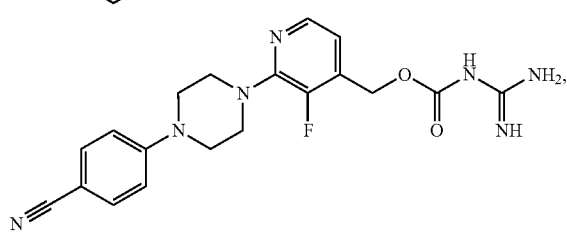
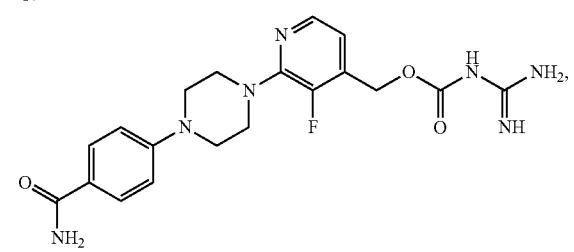
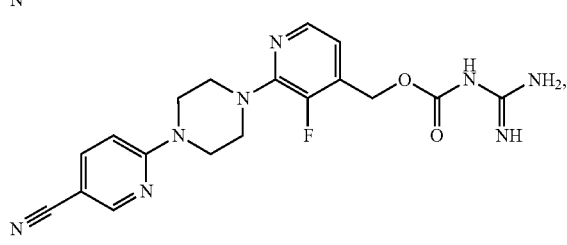
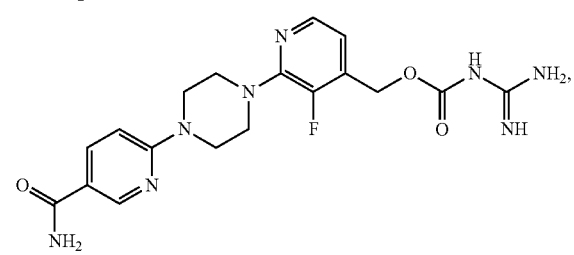

-continued

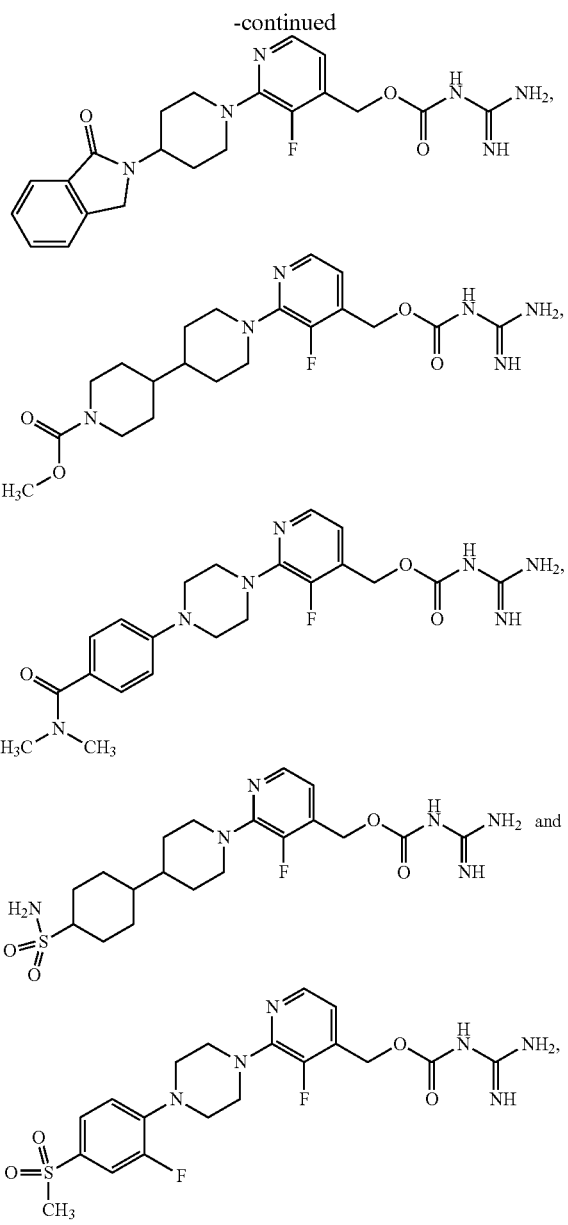

and the pharmaceutically acceptable salts thereof.

Particularly preferred compounds, including their tautomers and stereoisomers, the salts thereof, or any solvates or hydrates thereof, are described in the experimental section hereinafter.

The compounds according to the invention may be obtained using methods of synthesis which are known to the one skilled in the art and described in the literature of organic synthesis. Preferably, the compounds are obtained analogously to the methods of preparation explained more fully hereinafter, in particular as described in the experimental section.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embraces both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refers to the inhibition of AOC3 with one or more compounds of the present invention.

The terms "mediated" or "mediating" or "mediate", as used herein, unless otherwise indicated, refers to the (i) treatment, including prevention the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

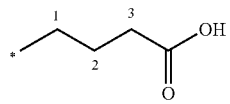

wherein the carboxy group is attached to the third carbon atom of the propyl group. The terms "1-methylpropyl-", "2,2-dimethylpropyl-" or "cyclopropylmethyl-" group represent the following groups:

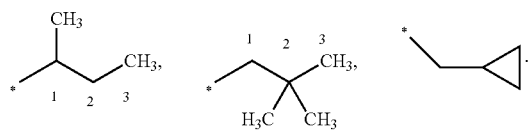

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

In the following the term bicyclic includes spirocyclic.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1.]octyl, spiro[4.5]decyl, norpinyl, norbonyl, norcaryl, adamantyl, etc.

Many of the terms given above may be used repeatedly in the definition of a formula or group and in each case have one of the meanings given above, independently of one another.

All rests and substituents as defined hereinbefore and hereinafter may be substituted with one or more F atoms.

Pharmacological Activity

The activity of the compounds of the invention may be demonstrated using the following AOC3 assay:

Biochemical Assay

The MAO-Glo™ Assay (commercial available from PROMEGA, # V1402) provides a sensitive method for the measurement of monoamine oxidase (MAO) activity (Valley, M. P. et al., 2006, Anal. Biochem. 359: 238-246) from a variety of tissues, biofluids or recombinant expressed or purified enzymes. As substrate a derivate of the beetle luciferin ((4S)-4,5-dihydro-2-(6-hydroxybenzothiazolyl)-4-thiazole-carboxylic acid) is used, which is oxidized at a primary amine moiety. After a spontaneous elimination and a catalyzed esterase reaction, the turnover of the luciferine by the luciferase is recorded as a signal of AOC3 activity.

For the determination of AOC3 activity or compound inhibition potency, the compound inhibitors are dissolved in DMSO and adjusted to the respective assay concentration with reaction buffer (50 mM HEPES, 5 mM KCl, 2 mM CaCl2, 1.4 mM MgCl2, 120 mM NaCl, 0.001% (v/v) Tween 20, 100 μM TCEP, pH 7.4). An aliquot of 3 μL of the compound dilution is added to a 384 well plate (Optiplate, PS, flat bottom, white, PERKIN ELMER, #6007290) with a final DMSO concentration of 6.6%. Recombinant CHO cells, overexpressing the human (1500 cells/well), mouse (1000 cells/well) or rat (500 cells/well) AOC3 enzyme are diluted in reaction buffer and added in a volume of 15 μL to the wells. After incubation for 20 minutes at 37° C., 2 µL of MAO substrate (dissolved in DMSO at 16 mM, adjusted to assay concentration in reaction buffer to a final assay concentration of 20 µM) is added and further incubated for 60 minutes at 37° C. The turnover of the substrate is determined by the addition of 20 µL of the detection-mix which was generated by the addition of reconstitution buffer with esterase (PROMEGA, # V1402) to the luciferine detection reagent (PROMEGA, # V1402). After an incubation period of 20 minutes, the luminescent signal is measured with Envision 2104 Multilabel Reader (PERKIN ELMER).

Alternative assays for the determination of the AOC3 enzymatic activity could be the extraction of 14C-labelled benzylamine reaction product or the Amplex Red Monoamine Oxidase reaction (Molecular Probes, Netherlands) as described in Gella et al. (Gella, A. et al., 2013, J. Neural Transm. 120: 1015-1018).

The compounds of general formula (I) according to the invention for example have $IC_{50}$ values below 5000 nM, particularly below 1000 nM, preferably below 300 nM, most preferably below 100 nM.

In the following table the activity expressed as $IC_{50}$ (nM) of compounds according to the invention is presented wherein the $IC_{50}$ values are determined in the MAO-Glo™ AOC3 assay as described hereinbefore. The term "Example" refers to the example numbers according to the following experimental section.

TABLE 1

Biological data of the compounds of the present invention as obtained in the MAO-Glo ™ assay.

| # | AOC3 $IC_{50}$ |
|---|---|
| 1.001 | 98 nM |
| 1.002 | 172 nM |
| 1.003 | 16 nM |
| 1.004 | 38 nM |
| 1.005 | 17 nM |
| 1.006 | 18 nM |
| 1.007 | 96 nM |
| 1.008 | 15 nM |
| 1.009 | 41 nM |
| 1.010 | 3 nM |
| 1.011 | 3 nM |
| 1.012 | 62 nM |
| 1.013 | 22 nM |
| 1.014 | 41 nM |
| 1.015 | 17 nM |
| 1.016 | 10 nM |
| 1.017 | 3 nM |
| 1.018 | 17 nM |
| 1.019 | 84 nM |
| 1.020 | 35 nM |
| 1.021 | 26 nM |
| 1.022 | 49 nM |
| 1.023 | 8 nM |
| 1.024 | 18 nM |
| 1.025 | 92 nM |
| 1.026 | 111 nM |
| 1.027 | 2 nM |
| 1.028 | 10 nM |
| 1.029 | 9 nM |
| 1.030 | 23 nM |
| 1.031 | 9 nM |
| 1.032 | 11 nM |
| 1.033 | 6 nM |
| 1.034 | 58 nM |
| 1.035 | 14 nM |
| 1.036 | 7 nM |
| 1.037 | 9 nM |
| 1.038 | 14 nM |
| 1.039 | 2 nM |
| 1.040 | 7 nM |
| 1.041 | 9 nM |
| 1.042 | 28 nM |
| 1.043 | 13 nM |
| 1.044 | 9 nM |
| 1.045 | 24 nM |
| 1.046 | 128 nM |
| 1.047 | 8 nM |
| 1.048 | 95 nM |
| 1.049 | 22 nM |
| 1.050 | 2 nM |
| 1.051 | 2 nM |
| 1.052 | 84 nM |
| 1.053 | 83 nM |
| 1.054 | 1 nM |
| 1.055 | 2 nM |
| 1.056 | 4 nM |
| 1.057 | 3 nM |
| 1.058 | 4 nM |
| 1.059 | 16 nM |
| 1.060 | 217 nM |
| 1.061 | 8 nM |
| 1.062 | 11 nM |
| 1.063 | 13 nM |
| 1.064 | 6 nM |
| 1.065 | 5 nM |
| 1.066 | 278 nM |
| 1.067 | 5 nM |
| 1.068 | 7 nM |
| 1.069 | 15 nM |
| 1.070 | 77 nM |
| 1.071 | 8 nM |
| 1.072 | 4 nM |
| 1.073 | 10 nM |
| 1.074 | 7 nM |
| 1.075 | 14 nM |
| 1.076 | 39 nM |
| 1.077 | 7 nM |
| 1.078 | 9 nM |
| 1.079 | 11 nM |
| 1.080 | 86 nM |
| 1.081 | 22 nM |
| 1.082 | 2 nM |
| 1.083 | 4 nM |
| 1.084 | 3 nM |
| 1.085 | 4 nM |
| 1.086 | 7 nM |
| 1.087 | 12 nM |
| 1.088 | 48 nM |
| 1.089 | 4 nM |
| 1.090 | 10 nM |
| 1.091 | 7 nM |
| 1.092 | 9 nM |
| 1.093 | 17 nM |
| 1.094 | 14 nM |
| 1.095 | 3 nM |
| 1.096 | 12 nM |
| 1.097 | 11 nM |
| 1.098 | 15 nM |
| 1.099 | 5 nM |
| 1.100 | 5 nM |
| 1.101 | 7 nM |
| 1.102 | 65 nM |
| 1.103 | 8 nM |
| 1.104 | 9 nM |
| 1.105 | 31 nM |
| 1.106 | 6 nM |

A comparison between compounds of the present invention and the corresponding phenyl analogues of EP 2695 881 shows that the compounds of the present invention are equally effective as AOC3 inhibitors than the prior art compounds.

TABLE 2

Comparative biological data as obtained in the MAO-Glo ™ assay.

| Compounds of the present invention | | | Compounds of EP 2 695 881 | | |
|---|---|---|---|---|---|
| Ex. No. | structure | IC$_{50}$ [nM] | Ex. (page) | structure | IC$_{50}$ [nM] |
| 1.067 | *(structure)* | 4.6 | 57 (227) | *(structure)* | 3.9 |
| 1.072 | *(structure)* | 4.1 | 126 (235) | *(structure)* | 3.9 |

TABLE 2-continued

Comparative biological data as obtained in the MAO-Glo™ assay.

| Compounds of the present invention | | | Compounds of EP 2 695 881 | | |
|---|---|---|---|---|---|
| Ex. No. | structure | IC$_{50}$ [nM] | Ex. (page) | structure | IC$_{50}$ [nM] |
| 1.084 | [structure] | 2.8 | –(–) phenyl-analogue of example 1-084 of the present invention | [structure] | 2.5 |

It has now been found out that, surprisingly, the compounds according to the present invention are metabolically more stable than the correspdonding prior art compounds, i.e. the replacement of the fluoro-substituted phenyl moiety (adjacent to the guanidine function) by a fluoro-substituted pyridinyl moiety results in metabolically more stable compounds. The metabolic stability was testet according to the following assay:

Metabolic Stability Assay

The metabolic degradation of the test compound is assayed in a hepatocyte suspension. Hepatocytes (typically cryopreserved) are incubated in an appropriate buffer system (e.g. Dulbecco's modified eagle medium plus 3.5 µg glucagon/500 mL, 2.5 mg insulin/500 mL and 3.75 mg/500 mL hydrocortison) containing 5% species serum. Following a (typically) 30 min preincubation in an incubator (37° C., 10% CO2) 5 µl of test compound solution (80 µM; from 2 mM in DMSO stock solution diluted 1:25 with medium) are added into 395 µl hepatocyte suspension (cell density in the range 0.25-5 Mio cells/mL, typically 1 Mio cells/mL; final concentration of test compound 1 µM, final DMSO concentration 0.05%). The cells are incubated for six hours (incubator, orbital shaker) and samples (25 µl) are taken at 0, 0.5, 1, 2, 4 and 6 hours. Samples are transferred into acetonitrile and pelleted by centrifugation (5 min). The supernatant is transferred to a new 96-deepwell plate, evaporated under nitrogen and resuspended. Decline of parent compound is analyzed by HPLC-MS/MS CLint is calculated as follows CL_INTRINSIC=Dose/ AUC=(C0/CD)/(AUD+clast/k)×1000/60. C0: initial concentration in the incubation [µM], CD: cell density of vital cells [10e6 cells/mL], AUD: area under the data [µM×h], clast: concentration of last data point [µM], k: slope of the regression line for parent decline [h-1].

The calculated in vitro hepatic intrinsic clearance can be scaled up to the intrinsic in vivo hepatic Clearance and used to predict hepatic in vivo blood clearance (CL) by the use of a liver model (well stirred model). CL_INTRINSIC_IN-VIVO [ml/min/kg]=(CL_INTRINSIC [µL/min/10e6 cells]× hepatocellularity [10e6 cells/g liver]×liver factor [g/kg bodyweight])/1000 CL [ml/min/kg]=CL_INTRINSIC_IN-VIVO [ml/min/kg]×hepatic blood flow [ml/min/kg]/ (CL_INTRINSIC_INVIVO [ml/min/kg]+hepatic blood flow [ml/min/kg])

Surprisingly, it tourned out that the replacement of a single atom, namely of carbon atom in the fluoro-substituted phenyl moiety by a nitrogen atom, leads to a significantly enhanced metabolic stability, as illustrated by the following comparative examples. An enhanced metabolic stability in a magnitude as shown below, i.e. an improvement of factor 2 to 3, enables a less frequent dosing (e.g. once daily vs. twice daily) and lower doses of the claimed compounds as compared to the corresponding phenyl analogues.

TABLE 3

Comparative Biological data as obtained in the metabolic stability assay.

| Compounds of the present invention | | | Compounds of EP 2 695 881 | | |
|---|---|---|---|---|---|
| Ex. No. | structure | $Q_H$ [%] | Ex. (page) | structure | $Q_H$ [%] |
| 1.067 | | 10 | 57 (227) | | 20 |
| 1.072 | | 3.7 | 126 (235) | | 11 |

TABLE 3-continued

Comparative Biological data as obtained in the metabolic stability assay.

| Compounds of the present invention | | | Compounds of EP 2 695 881 | | |
|---|---|---|---|---|---|
| Ex. No. | structure | $Q_H$ [%] | Ex. (page) | structure | $Q_H$ [%] |
| 1.084 | 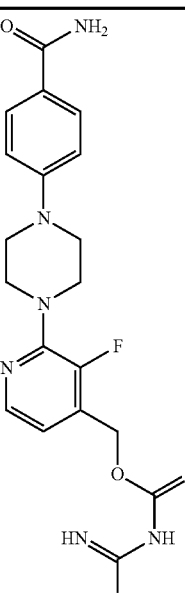 | 23 | -(-) phenyl-analogue of example 1-084 of the present invention | 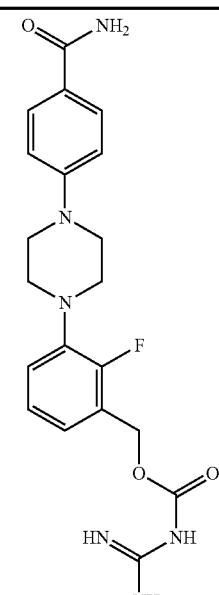 | 47 |

Furthermore, the metabolic stability has been confirmed for compounds according to the invention as outlined in Table 4.

TABLE 4

Biological data as obtained in the metabolic stability assay.

| # | $Q_H$ |
|---|---|
| 1.010 | 16% |
| 1.011 | <4% |
| 1.016 | 6% |
| 1.017 | 6% |
| 1.023 | 14% |
| 1.027 | 9% |
| 1.031 | 23% |
| 1.033 | 4% |
| 1.036 | 16% |
| 1.037 | 20% |
| 1.039 | <4% |
| 1.040 | 7% |
| 1.041 | 12% |
| 1.044 | 56% |
| 1.047 | <4% |
| 1.050 | 10% |
| 1.051 | 20% |
| 1.054 | 14% |
| 1.055 | 16% |
| 1.056 | 12% |
| 1.058 | 18% |
| 1.061 | 13% |
| 1.064 | 14% |
| 1.065 | 40% |
| 1.067 | 23% |
| 1.068 | 23% |
| 1.072 | 4% |
| 1.074 | 24% |
| 1.077 | 30% |
| 1.078 | 14% |
| 1.083 | 11% |

TABLE 4-continued

Biological data as obtained in the metabolic stability assay.

| # | $Q_H$ |
|---|---|
| 1.084 | 10% |
| 1.085 | 85% |
| 1.086 | 11% |
| 1.089 | 8% |
| 1.091 | 7% |
| 1.092 | 92% |
| 1.095 | 15% |
| 1.099 | 9% |
| 1.100 | 9% |
| 1.101 | <4% |
| 1.103 | <4% |
| 1.104 | 5% |
| 1.106 | 8% |

In Vivo Clearance Experiment

Bile flow is continuously collected from animal for 4 hours, including the 1 hour post-surgery recovery period. For short biliary excretion study, blood samples are taken at 0, 5 and 180 min and bile samples collection intervals are: 10 min before dosing and 0-180 min. All blood and bile samples are collected from 2 rats and are not pooled. Bile is kept at 4° C. during the collecting intervals and immediately frozen in dry ice after the collecting period is over.

Moreover, the heteroaryl derivatives according to the present invention show significantly reduced biliary clearance as compared to the phenyl compounds described in the prior art. As biliary clearance is expected to be impaired in patients with liver diseases (Clarke J. D. et. al J. Pharm. Exp. Ther. 348:452-458; Ferslew B. C. et al. Clin. Pharm. & Ther. Vol 97(4) XX), a reduced biliary clearance results in a better predictibitlity of the pharmacokinetics and assessment of safety margins in this patient population.

TABLE 5

Biological data as obtained in the in vivo clearance experiment.

| Compounds of the present invention | | | Compounds of EP 2 695 881 | | |
|---|---|---|---|---|---|
| Ex. No. | structure | Cl [%] | Ex. (page) | structure | Cl [%] |
| 1.072 | (structure) | 1.2 | 559 (293) | (structure) | 10.3 |
| 1.084 | (structure) | 2.2 | 11 (221) | (structure) | 22.4 |

(Remark: In view of the fact that biliary clearance can only be tested in vivo, only a limited amount of data was generated in careful consideration of animal protection and general ethical rules.)

In view of their ability to inhibit AOC3, the compounds of general formula (I) according to the invention and the corresponding salts thereof are theoretically suitable for the treatment, including preventative treatment of all those diseases or conditions which may be affected or which are mediated by the inhibition of AOC3 activity.

Accordingly, the present invention relates to a compound of general formula (I) as a medicament.

Furthermore, the present invention relates to the use of a compound of general formula (I) for the treatment and/or prevention of diseases or conditions which are mediated by the inhibition of AOC3 in a patient, preferably in a human.

In yet another aspect the present invention relates a method for treating, including preventing a disease or condition mediated by the inhibition of AOC3 in a mammal that includes the step of administering to a patient, preferably a human, in need of such treatment a therapeutically effective amount of a compound of the present invention, or a pharmaceutical composition thereof.

Diseases and conditions mediated by inhibitors of AOC3 embrace NASH (non-alcoholic steatohepatitis), retinopathy or nephropathy.

According to one aspect the compounds of the present invention are particularly suitable for treating inflammatory diseases, such as vascular inflammatory diseases, arthritis, acute and chronic joint inflammation; eczema, such as atopic eczema, psoriasis ulcerative and rheumatoid psoriasis; pain, particularly musculoskeletal or nociceptive pain; inflammatory bowel disease, particularly non-infectious inflammatory bowel disease; multiple sclerosis; scleroderma, pulmonary diseases such as respiratory distress syndrome, asthma, pulmonary and iodiopathic fibrosis, chronic obstructive pulmonary disease (COPD) and idiopathic inflammatory disease; nephropathy, diabetic proteinuria, kidney fibrosis; diabetic retinopathy or diabetic oedema such as macular diabetic oedema; cancer, particularly melanoma and lymphoma; primary sclerosing cholangitis, unspecified Colitis, rheumatoid Crohn's disease Colitis; biliary tract diseases, non-alcoholic steatohepatitis (NASH), non-alcoholic fatty liver disease (NAFLD), liver fibrosis, liver cirrhosis; ulcerative reperfusion injury, cerebral ischaemia and transplant rejection.

According to another aspect the compounds of the present invention are particularly suitable for treating inflammatory diseases, such as vascular inflammatory diseases, arthritis and inflammatory bowel disease, particularly non-infectious inflammatory bowel disease; pulmonary and iodiopathic fibrosis; diabetic retinopathy or diabetic oedema such as macular diabetic oedema; primary sclerosing cholangitis, unspecified Colitis, rheumatoid Crohn's disease Colitis; biliary tract diseases, non-alcoholic steatohepatitis (NASH), non-alcoholic fatty liver disease (NAFLD), liver fibrosis, and liver cirrhosis.

The dose range of the compounds of general formula (I) applicable per day is usually from 0.001 to 10 mg per kg body weight of the patient, preferably from 0.01 to 8 mg per kg body weight of the patient. Each dosage unit may conveniently contain 0.1 to 1000 mg of the active substance, preferably it contains between 0.5 to 500 mg of the active substance.

The actual therapeutically effective amount or therapeutic dosage will of course depend on factors known by those skilled in the art such as age and weight of the patient, route of administration and severity of disease. In any case the combination will be administered at dosages and in a manner which allows a therapeutically effective amount to be delivered based upon patient's unique condition.

Pharmaceutical Compositions

Suitable preparations for administering the compounds of formula (I) will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers.

Combination Therapy

The compounds of the invention may further be combined with one or more, preferably one additional therapeutic agent. According to one embodiment the additional therapeutic agent is selected from the group of therapeutic agents useful in the treatment of diseases or conditions associated with the metabolic syndrom, diabetes, obesity, cardiovascular diseases, NASH (non-alcoholic steatohepatitis), retinopathy and/or nephropathy.

Therefore a compound of the invention may be combined with one or more additional therapeutic agents selected from the group consisting of anti-obesity agents (including appetite suppressants), agents which lower blood glucose, anti-diabetic agents, agents for treating dyslipidemias, such as lipid lowering agents, anti-hypertensive agents, antiatherosclerotic agents, anti-inflammatory active ingredients, anti-fibrotic agents, agents for the treatment of malignant tumors, antithrombotic agents, anti-angiogenesis agents, agents for the treatment of heart failure and agents for the treatment of complications caused by diabetes or associated with diabetes.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment or prevention of diseases or conditions which may be affected or which are mediated by the inhibition of AOC3, in particular diseases or conditions as described hereinbefore and hereinafter.

In yet another aspect the present invention relates a method for treating, including preventing a disease or condition mediated by the inhibition of AOC3 in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Synthesis Schemes

Typical methods of preparing the compounds of the invention are described in the experimental section.

The potent inhibitory effect of the compounds of the invention can be determined by in vitro enzyme assays as described in the experimental section.

The compounds of the present invention may also be made by methods known in the art including those described below and including variations within the skill of the art.

Scheme 1:

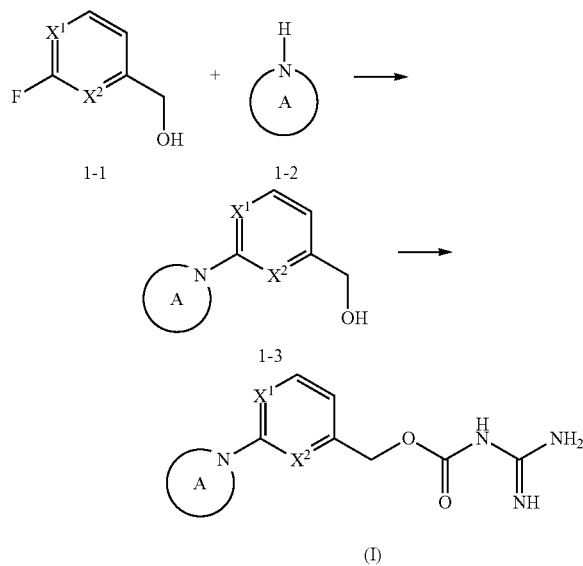

Compounds of the general formula (I), wherein $X^1$, $X^2$ and ring A are as previously defined, can be prepared via the process outlined in Scheme 1 using a compound of the general formula 1-1, wherein $X^1$, $X^2$ as well as ring A are as previously defined, with an cyclic amine 1-2, in presence of a base in appropriate solvents such as DMSO or NMP at a temperature between 0° C. and 150° C. As a base sodium $K_2CO_3$ or DIPEA may be used. The reaction of the benzylic alcohol of the general formula 1-3, wherein $X^1$, $X^2$ and ring A are as previously defined, in order to obtain a compound of the general formula (I), wherein $X^1$, $X^2$ and ring A are as previously defined, may be achieved via the acylation with CU followed by reaction with a guanidine salt in an appropriate solvent such as DMF. If reasonable, the reaction sequence to obtain compounds of the general formula (I) can also be reversed.

Scheme 2:

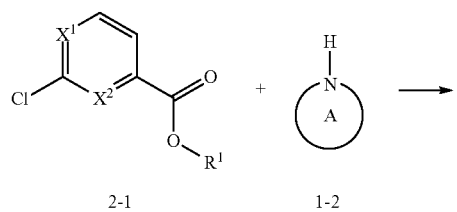

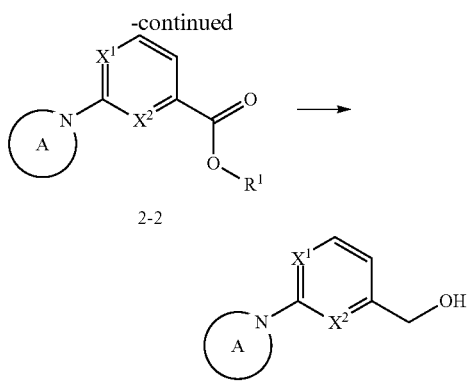

Intermediates of the general formula (1-3), wherein $X^1$, $X^2$ and ring A are as previously defined, can alternatively be prepared via the process outlined in Scheme 2 using a compound of the general formula 2-1, wherein $X^1$, $X^2$ as well as ring A are as previously defined and $R^1$ is $C_{1-4}$-alkyl, preferably methyl or ethyl with an cyclic amine 1-2, in presence of a base in appropriate solvents such as DMF at a temperature between 0° C. and 150° C. As a base DIPEA may be used. The reduction of the ester of the general formula 2-1, wherein $X^1$, $X^2$, $R^1$ and ring A are as previously defined, in order to obtain a compound of the general formula (1-3), wherein $X^1$, $X^2$ and ring A are as previously defined, may be achieved via reducing agents such as $LiAlH_4$ or $LiBH_4$ in an appropriate solvent such as THF.

Scheme 3:

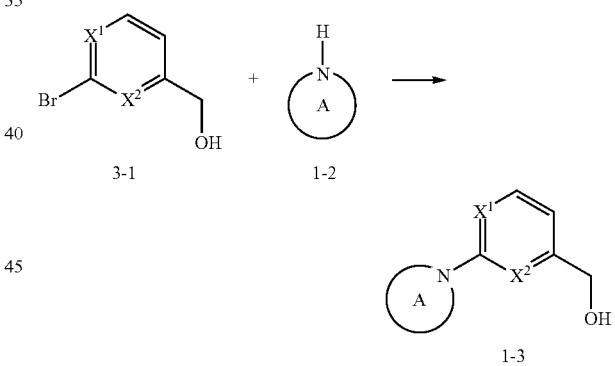

Alternatively, intermediates of the general formula (1-3), wherein $X^1$, $X^2$ and ring A are as previously defined, can be prepared via the process outlined in Scheme 3 using a compound of the general formula 3-1, wherein $X^1$, $X^2$ as well as ring A are as previously defined, with an cyclic amine 1-2, in presence of a suitable Pd-catalyst such as $Pd_2dba_3$, ligand such as 2-(di-tButylphosphino)biphenyl and base such as $NaO^tBu$ in appropriate solvents such as dioxane at a temperature between 50° C. and 100° C. as described by Buchwald et al. in Chem. Sci., 2011, 2, 27. Under certain circumstances, it may be advantageous to use a protection group for the primary alcohol such as tert-Butyl-dimethylsilyl.

The synthetic routes presented may rely on the use of protecting groups. For example, reactive groups present, such as hydroxy, carbonyl, carboxy, amino, alkylamino or imino, may be protected during the reaction by conventional protecting groups which are cleaved again after the reaction. Suitable protecting groups for the respective functionalities and their removal are well known to the one skilled in the art and are described in the literature of organic synthesis.

The compounds of general formula I may be resolved into their enantiomers and/or diastereomers as mentioned before. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned above.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

Experimental Part

The Examples that follow are intended to illustrate the present invention without restricting it. The terms "ambient temperature" and "room temperature" are used interchangeably and designate a temperature of about 20° C.

The hereinafter described compounds have been characterized through their characteristic mass after ionisation in a mass-spectrometer and their retention time on an analytical HPLC.

| List of Abbreviations | |
|---|---|
| ACN | Acetonitrile |
| AcOH | Acetic acid |
| aq. | Aqueous |
| BINAP | [1-(2-Diphenylphosphanyl-1-naphthyl)-2-naphthyl]-diphenyl-phosphane |
| Boc/BOC | Tert-butoxy-carbonyl- |
| ° C. | Degree celsius |
| CDI | Di(imidazol-1-yl)methanone |
| dba | Dibenzylideneacetone |
| DCM | Dichloromethane |
| DIPEA | N-ethyl-N-isopropyl-propan-2-amine |

-continued

| List of Abbreviations | |
|---|---|
| DMF | N,N-dimethylformamide |
| ESI-MS | Electrospray ionisation mass spectrometry |
| EtOAc/EE | Ethyl acetate |
| FC | Flash-cromatography, $SiO_2$ is used if no further details given |
| h | Hour |
| HPLC | High performance liquid chromatography |
| L | Liter |
| MeOH | Methanol |
| min | Minute |
| ml | Milliliter |
| NMP | N-Methyl-2-pyrrolidone |
| MS | Mass spectrum |
| MTBE | 2-Methoxy-2-methyl-propane |
| n.d. | Not determined |
| RT | Room temperature (about 20° C.) |
| $R_t$ | Retention time |
| TEA | Triethyl amine |
| TF/TFA | Trifluoroacetic acid |
| THF | Tetrahydrofuran |

HPLC-A: Agilent 1200 with DA- and MS-Detector, Sunfire C18_3.0×30 mm, 2.5 μm (Waters), 60° C.

| Time [min] | % Sol [H2O 0.1% TFA] | % Sol [Acetonitrile] | Flow [ml/min] |
|---|---|---|---|
| 0.0 | 97.0 | 3.0 | 2.2 |
| 0.2 | 97.0 | 3.0 | 2.2 |
| 1.2 | 0.0 | 100.0 | 2.2 |
| 1.25 | 0.0 | 100.0 | 3.0 |
| 1.4 | 0.0 | 100.0 | 3.0 |

HPLC-B: Waters Acquity with 3100 MS, XBridge C18_3.0×30 mm, 2.5 μm (Waters), 60° C.

| Time [min] | % Sol [$H_2O$ 0.1% $NH_4OH$] | % Sol [Acetonitrile] | Flow [ml/min] |
|---|---|---|---|
| 0.0 | 95.0 | 5.0 | 1.5 |
| 1.3 | 1.0 | 99.0 | 1.5 |
| 1.5 | 0.1 | 99.9 | 1.5 |
| 1.6 | 95.0 | 5.0 | 1.5 |

HPLC—C: Agilent 1200 with DA- and MS-detector, XBridge C18_3.0×30 mm, 2.5 μm (Waters), 60° C.

| Time [min] | % Sol [$H_2O$ 0.1% $NH_4OH$] | % Sol [Acetonitrile] | Flow [ml/min] |
|---|---|---|---|
| 0.0 | 97.0 | 3.0 | 2.2 |
| 0.2 | 97.0 | 3.0 | 2.2 |
| 1.2 | 0.0 | 100.0 | 2.2 |
| 1.25 | 0.0 | 100.0 | 3.0 |
| 1.4 | 0.0 | 100.0 | 3.0 |

HPLC-D: Agilent 1100 with DA- and MS-detector, Sunfire C18_3.0×30 mm, 3.5 μm (Waters), 60° C.

| Time [min] | % Sol [$H_2O$ 0.1% TFA] | % Sol [Acetonitrile] | Flow [ml/min] |
|---|---|---|---|
| 0.0 | 98.0 | 2.0 | 2.0 |
| 0.3 | 98.0 | 2.0 | 2.0 |
| 1.5 | 0.0 | 100.0 | 2.0 |
| 1.6 | 0.0 | 100.0 | 2.0 |

HPLC-E: Sunfire C18_2.1×30 mm, 2.5 μm (Waters), 60° C.

| Time [min] | % Sol [H₂O, 0.1% TFA] | % Sol [Acetonitrile] | Flow [ml/min] |
|---|---|---|---|
| 0.0 | 99 | 1 | 1.5 |
| 0.02 | 99 | 1 | 1.5 |
| 1.00 | 0 | 100 | 1.5 |
| 1.10 | 0 | 100 | 1.5 |

HPLC-F: Sunfire C18_3.0×30 mm, 2.5 μm (Waters), 60° C.

| Time [min] | % Sol [H₂O 0.1% TFA] | % Sol [Acetonitrile] | Flow [ml/min] |
|---|---|---|---|
| 0.0 | 98.0 | 2.0 | 2.0 |
| 1.2 | 0.0 | 100.0 | 2.0 |
| 1.4 | 0.0 | 100.0 | 2.0 |

HPLC-G: Waters Acquity with DA- and MS-Detector, XBridge C18_3.0×30 mm, 2.5 μm (Waters), 60° C.

| Time [min] | % Sol [H₂O 0.1% NH₄OH] | % Sol [Acetonitrile] | Flow [ml/min] |
|---|---|---|---|
| 0.0 | 98.0 | 2.0 | 2.0 |
| 1.2 | 0.0 | 100.0 | 2.0 |
| 1.4 | 0.0 | 100.0 | 2.0 |

HPLC-H: Agilent 1100 with DA- and MS-detector, XBridge C18_4.6×30 mm, 3.5 μm (Waters), 60° C.

| Time [min] | % Sol [H₂O 0.1% NH3] | % Sol [Acetonitrile] | Flow [ml/min] |
|---|---|---|---|
| 0.0 | 95.0 | 5.0 | 4.0 |
| 0.15 | 95.0 | 5.0 | 4.0 |
| 1.5 | 0.0 | 100.0 | 4.0 |
| 1.85 | 0.0 | 100.0 | 4.0 |

HPLC-1 Agilent 1100 with DA- and MS-detector, XBridge C18_4.6×30 mm, 3.5 μm (Waters), 60° C.

| Time [min] | % Sol [H₂O 0.1% NH3] | % Sol [Acetonitrile] | Flow [ml/min] |
|---|---|---|---|
| 0.0 | 50.0 | 50.0 | 4.0 |
| 0.15 | 50.0 | 50.0 | 4.0 |
| 1.5 | 0.0 | 100.0 | 4.0 |
| 1.85 | 0.0 | 100.0 | 4.0 |

I. 1 (2,3-difluoro-4-pyridyl)methanol

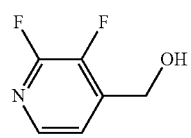

To a mixture of 1.0 g (6.1 mmol) 2,3-difluoropyridine-4-carboxylic acid and THF 1.09 g (6.7 mmol) CU is added and the mixture is stirred at RT for 1 h, then a solution of 0.35 g (9.15 mmol) NaBH₄ in 1.8 ml water is added dropwise and stirring is continued overnight. The reaction mixture is cooled in an ice bath, 3 ml 4M HCl are added and the mixture is diluted with EtOAc and water. The aqueous layer is separated and extracted with EtOAc. The organic layers are pooled, washed with water and evaporated. The crude product is purified by HPLC.

Yield: 392 mg (44%), ESI-MS: m/z=146 (M+H)⁺, R_f(HPLC): 0.60 min (HPLC-A)

I. 2 (2-bromo-3-fluoro-4-pyridyl)methanol

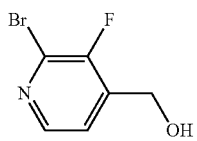

A mixture of 0.97 g (4.4 mmol) 2-bromo-3-fluoro-pyridine-4-carbaldehyde hydrate and MeOH is cooled in an ice bath and 215 mg (5.7 mmol) NaBH₄ is added and the mixture is warmed to RT and stirred for 2 h. The mixture is diluted with EtOAc and water and the aqueous layer is separated and extracted with EtOAc. The organic layers are pooled, washed with brine, dried over MgSO₄ and evaporated.

Yield: 830 mg (92%), ESI-MS: m/z=206 (M+H)⁺, R_f(HPLC): 0.60 min (HPLC-H)

I. 3 (2-bromo-3-fluoro-4-pyridyl)methoxy-tert-butyl-dimethyl-silane

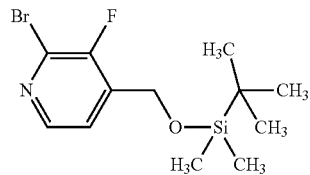

To a mixture of 820 mg of Intermediate I.2 (3.98 mmol) and DMF, 540 mg imidazole (7.93 mmol) and 630 mg tert-butyl-chloro-dimethyl-silane (4.18 mmol) are added and the reaction mixture is stirred overnight at RT. Then diluted with EtOAc and washed with water and brine, dried over MgSO₄ and evaporated.

Yield: 1.2 g (97%), ESI-MS: m/z=320 (M+H)⁺, R_f(HPLC): 1.01 min (HPLC-I)

The following Intermediates are obtained according to the given references.

| # | Structure/Reference |
|---|---|
| I.60 | (structure) Br-pyridine-CH₂OH<br>WO2009/120789 |

| # | Structure/Reference |
|---|---|
| I.61 | 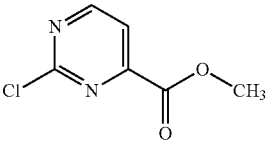<br>US2007/225271 |

II. 1 (3-fluoro-2-piperazin-1-yl-4-pyridyl)methanol

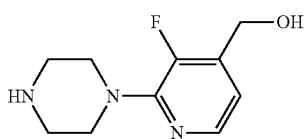

Step 1: A mixture of 10 g (69 mmol) intermediate I.1, 20.5 g (110 mmol) tert-butyl piperazine-1-carboxylate, 1.5 ml (90 mmol) DIPEA and DMSO is stirred at 100° C. for 16 h. The reaction mixture is cooled to RT, diluted with water and extrexted with EtOAc. The organic phases are pooled, washed with brine, dried over $Na_2SO_4$ and concentrated. The crude product was puridied by FC, giving rise to 14 g (65%) tert-butyl 4-[3-fluoro-4-(hydroxymethyl)-2-pyridyl]piperazine-1-carboxylate.

Step 2: A mixture of 9 g (28.9 mmol) tert-butyl 4-[3-fluoro-4-(hydroxymethyl)-2-pyridyl]piperazine-1-carboxylate and dioxane was cooled to 0° C. and 100 ml (400 mmol) 4 M HCl in dioxane was added and the reaction mixture is stirred at 0° C. for 1 h. The precipitate is filtered off, triturated with pentane and dried giving rise to (3-fluoro-2-piperazin-1-yl-4-pyridyl)methanol as hydrochloride.

Yield: 6.5 g (91%), ESI-MS: m/z=211 (M+H)$^+$, $R_t$(HPLC): 0.61 min (HPLC—C)

The following Intermediates are obtained according to the given references.

| # | Structure/Reference |
|---|---|
| III.1 | 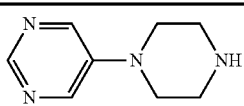<br>US2005/176722 |
| III.2 | 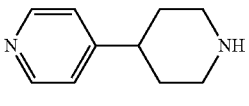 [SMILES: c1cc(C2CCNCC2)ccn1]<br>US2009/176775 |
| III.3 | 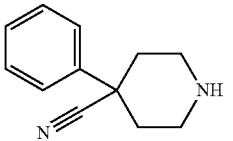 [SMILES: N#CC1(c2ccccc2)CCNCC1]<br>WO2004/113275 |
| III.4 | 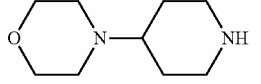 [SMILES: C1CC(N2CCOCC2)CCN1]<br>US2008/45705 |
| III.5 | 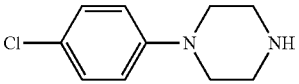 [SMILES: Clc1ccc(N2CCNCC2)cc1]<br>WO2013/177253 |
| III.6 | 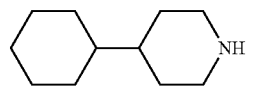 [SMILES: C1CCC(C2CCNCC2)CC1]<br>US2004/242572 |
| III.7 | 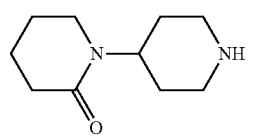<br>WO2013/142307 |
| III.8 | 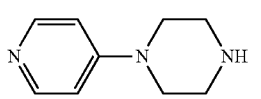<br>U.S. Pat. No. 4,355,031 |
| III.9 | 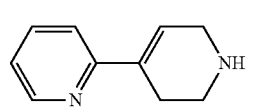<br>WO2013/83741 |
| III.10 | 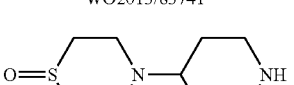<br>WO2012/101013 |
| III.11 | 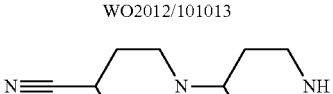<br>US2007/72847 |
| III.12 | 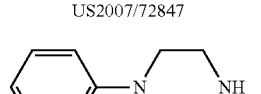<br>WO2011/72174 |
| III.13 | 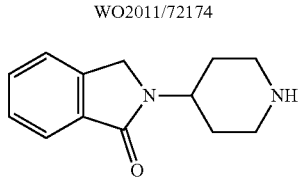<br>US2008/249101 |

| # | Structure/Reference |
|---|---|
| III.14 | 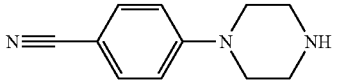<br>U.S. Pat. No. 5,442,064 |
| III.15 | 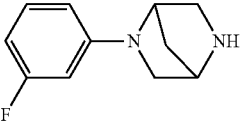 [SMILES: Fc1cccc(N2CC3CC2CN3)c1]<br>J. Med. Chem., 2007, 50, 3627 |
| III.16 | 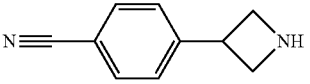 [SMILES: N#Cc1ccc(C2CNC2)cc1]<br>WO2014/8197 |
| III.17 | 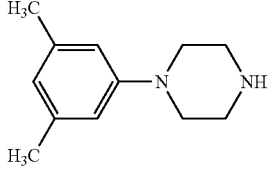<br>J. Med Chem., 1965, 8, 104 |
| III.18 | 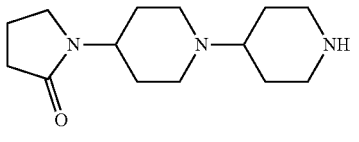 [SMILES: O=C1CCCN1C1CCN(C2CCNCC2)CC1]<br>WO2010/70032 |
| III.19 | 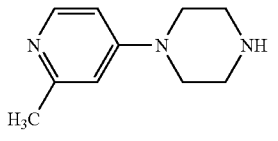<br>U.S. Pat. No. 4,788,196 |
| III.20 | 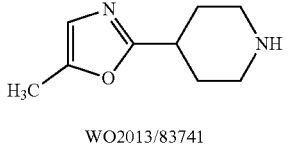<br>WO2013/83741 |
| III.21 | 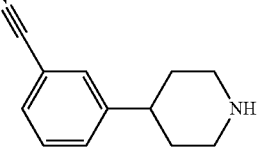<br>WO2004/92124 |
| III.22 | 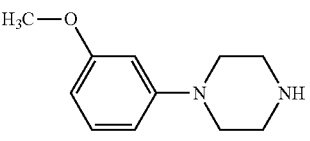 |

| # | Structure/Reference |
|---|---|
| | U.S. Pat. No. 5,929,281 |
| III.24 | 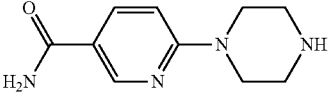<br>Commercially available from Enamine, 23 A. Motrosova Street Kiev 01103 UKRAINE |
| III.25 | 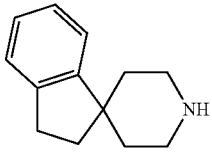 [SMILES: c1ccc2c(c1)CCC21CCNCC1]<br>WO2007/38459 |
| III.26 | 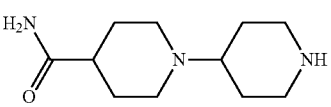<br>Commercially available from Matrix Scientific P.O. Box 25067 Columbia, SC 29224-5067 USA |
| III.27 | 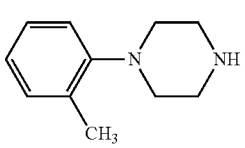<br>U.S. Pat. No. 5,929,281 |
| III.28 | 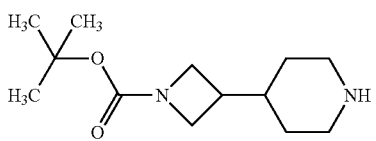 [SMILES: CC(C)(C)OC(=O)N1CC(C2CCNCC2)C1]<br>US2013/102584 |
| III.29 | 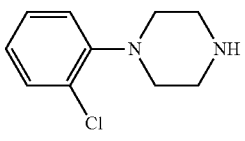 [SMILES: Clc1ccccc1N1CCNCC1]<br>U.S. Pat. No. 2,833,770 |
| III.30 | 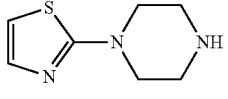<br>US2010/152158 |
| III.31 | 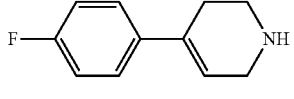<br>WO2004/113275 |

-continued
| # | Structure/Reference |
|---|---|
| III.32 | 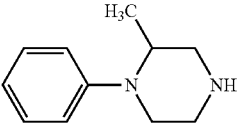<br>U.S. Pat. No. 6,825,200 |
| III.33 | 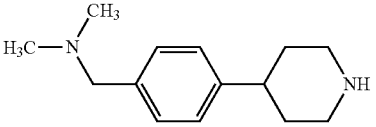 [SMILES: CN(C)Cc1ccc(C2CCNCC2)cc1]<br>US2004/242572 |
| III.34 | 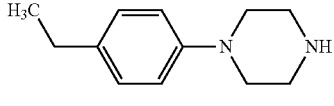<br>WO2010/81851 |
| III.35 | 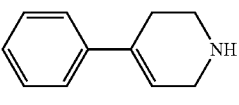<br>WO2004/113275 |
| III.36 | 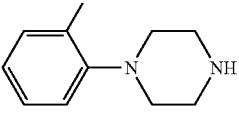<br>U.S. Pat. No. 5,086,055 |
| III.37 | 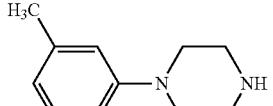<br>US2002/19389 |
| III.38 | 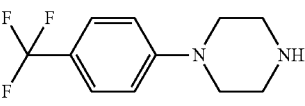 [SMILES: FC(F)(F)c1ccc(N2CCNCC2)cc1]<br>US2005/250791 |
| III.39 | 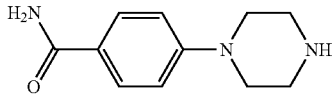<br>EP 277725 |
| III.40 | 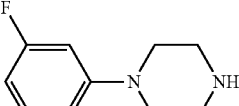<br>WO 2013051672 |
| III.41 | 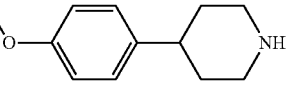<br>WO 2014096378 |
| III.42 | 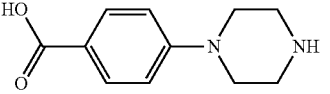<br>WO2001/058886 |
| III.43 | <br>WO 2009091388 |
| III.44 | 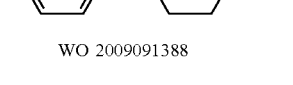<br>WO 2004046107 |
| III.45 | 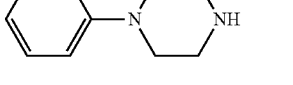<br>WO 2011028947 |
| III.46 | 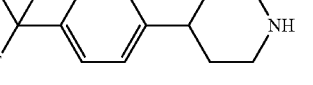<br>WO 2012064569 |
| III.47 | 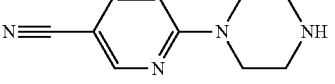<br>WO 2007087135 |
| III.48 | 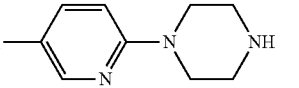<br>WO 2014096378 |
| III.49 | 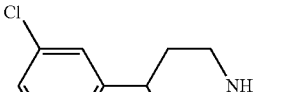<br>WO 2014096378 |
| III.50 | 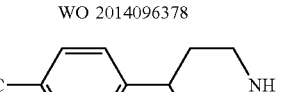<br>WO 2014008197 |

| # | Structure/Reference |
|---|---|
| III.51 | 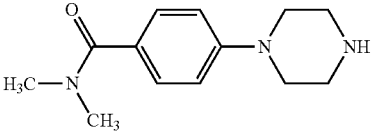<br>WO 2005100365 |
| III.52 | 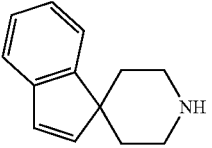 [SMILES: C1=CC2(CCNCC2)c2ccccc21]<br>U.S. Pat. No. 5,693,643 |
| III.53 | 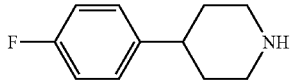 [SMILES: Fc1ccc(C2CCNCC2)cc1]<br>WO2004/41279 |
| III.54 | 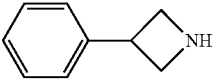<br>US2008/214520 |
| III.55 | 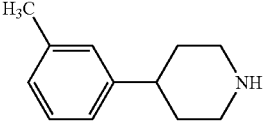<br>WO2008/12622 |
| III.56 | 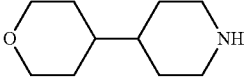 [SMILES: C1CC(C2CCOCC2)CCN1]<br>EP992493 |
| III.57 | 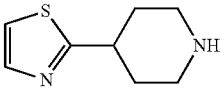<br>WO2004/41777 |
| III.59 | 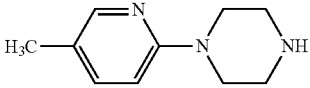<br>WO2006/89664 |
| III.60 | 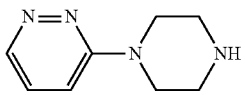<br>US2005/176722 |
| III.61 | 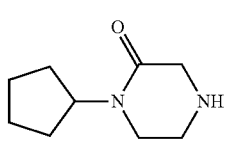 [SMILES: O=C1CNCCN1C1CCCC1]<br>WO2011/97491 |
| III.62 | 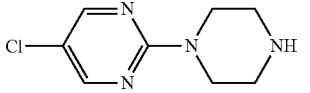 [SMILES: Clc1cnc(N2CCNCC2)nc1]<br>US2014/228286 |
| III.63 | 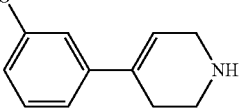<br>*Bioorg. Med. Chem. Lett.*, 2003, 13(22), 3951 |
| III.64 | 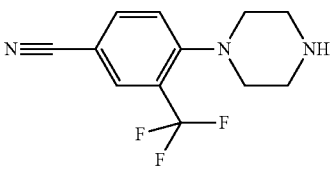 [SMILES: N#Cc1ccc(N2CCNCC2)c(C(F)(F)F)c1]<br>*Adv. Synth. Cat.*, 2006, 348 (1-2), 23 |
| III.65 | 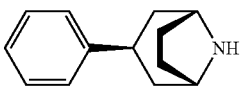<br>US2012/225876 |
| III.66 | 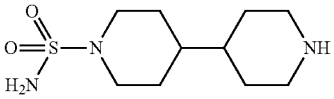<br>US2005/256099 |
| III.67 | 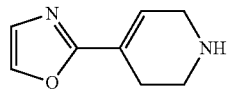 [SMILES: C1=C(c2ncco2)CCNC1]<br>WO2013/83741 |
| III.68 | 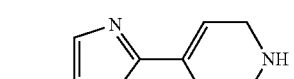<br>WO2013/83741 |
| III.69 | 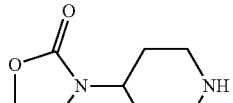<br>WO2005/12296 |
| III.70 | 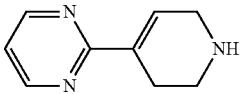<br>WO2013/83741 |

| # | Structure/Reference |
|---|---|
| III.71 | WO2013/83741 |
| III.72 | US2004/220194 |
| III.73 | US2005/277647 |
| III.74 | US2010/190771 |
| III.76 | WO2013/92976 |
| III.77 | WO2013/87738 |
| III.78 | WO2006/106423 |
| III.80 | WO2006/71730 |
| III.81 | WO2006/47415 |
| III.82 | US2010/331307 |
| III.83 | WO2013/177253 |
| III.84 | Tet. Lett., 2000, 41(16), 2881 |
| III.85 | US2004/242572 |
| III.86 | U.S. Pat. No. 5,086,055 |
| III.87 | J. Med. Chem., 1965, 8, 104 |

III. 160 2-fluoro-5-(1,2,3,6-tetrahydropyridin-4-yl)pyrimidine

A mixture of 1.0 g (7.32 mmol) 2-chloro-5-fluoropyrimidine, 2.7 g (8.35 mmol) tert-butyl 4-(4,4,5,5-tetramethyl-1,3,2-dioxaborolan-2-yl)-3,6-dihydro-2H-pyridine-1-carboxylate, 342 mg (0.29 mmol) tetrakis(triphenylphosphine)palladium(0), 7.3 ml (14.6 mmol) 2M $Na_2CO_3$ solution and dioxane is heated to 140° C. for 15 min using a microwave reactor. The reaction mixture is cooled to RT and evaporated. DCM and water are added to the residual, the organic phase is separated and evaporated. The crude product is purified by HPLC and 20 ml (80 mmol) 4 M HCl in dioxane is added and the mixture was stirred at RT for 2 h. The precipitate is filtered off, washed with dioxane and dried.

Yield as HCl-salt: 617 mg (40%), ESI-MS: m/z=180 $(M+H)^+$

III. 162 1-[4-(azetidin-3-yl)-1-piperidyl]ethanone

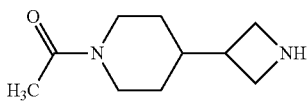

A mixture of 11.2 g (46.7 mmol) tert-butyl 3-(4-piperidyl) azetidine-1-carboxylate, 25 ml (178.9 mmol) Et₃N and DCM is cooled to 0° C. and 4.9 ml (51.8 mmol) acetic anhydride in 15 ml DCM is added slowly and the mixture is stirred for 20 min, then warmed to RT and stirred for additional 3 h. The reaction mixture is washed with saturated NaHCO₃ solution, 1 M HCl and brine, dried with MgSO₄ and evaporated. DCM and 1.37 ml (17.76 mmol) TFA are added and the mixture is stirred at RT overnight. The reaction mixture is diluted with DCM and cooled to 0° C. 4.5 ml (17.8 mmol) 4 M NaOH solution is added slowly, the aqueous phase is separated, diluted with K₂CO₃ solution and extracted with DCM. The organic phases are pooled, dried with MgSO₄ and evaporated giving rise to 12.6 g tert-butyl 3-(1-acetyl-4-piperidyl)azetidine-1-carboxylate.

A mixture of 6.7 g (23.7 mmol) tert-butyl 3-(1-acetyl-4-piperidyl)azetidine-1-carboxylate and DCM is cooled to 0° C. and 22 ml (287.3 mmol) TFA are added and the mixture is warmed to RT and stirred for 2 h. The reaction mixture is diluted with DCM and cooled to 0° C. 71.8 ml (287.3 mmol) 4 M NaOH solution is added slowly, the aqueous phase is separated, saturated with K₂CO₃ and extracted with DCM. The organic phases are pooled, dried with MgSO₄ and evaporated.

Yield: 2.1 g (49%), ESI-MS: m/z=183 (M+H)⁺

III. 163 2-methoxy-5-piperazin-1-yl-pyrimidine

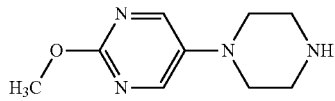

To a mixture of 2 g (10.6 mmol) 5-bromo-2-methoxypyrimidine, 2 g (10.8 mmol) tert-butyl piperazine-1-carboxylate, 1.4 g (14.9 mmol) sodium tert-butylate, 177 mg (0.28 mmol) BINAP and toluene 128 mg (0.14 mmol) Pd₂dba₃ is added and the reaction mixture heated to 80° C. for 4 h, then cooled to RT and stirred overnight and diluted with EtOAc and water. The organic phase is separated, washed with water and brine, dried over MgSO₄ and evaporated and the residual is purified by FC. DCM is added and the mixture cooled to 0° C. 3.4 ml (43.5 mmol) TFA are added and the mixture is warmed to RT and stirred for 1.5 h. The reaction mixture is diluted with EtOAc and evaporated. EtOAc and 10% K₂CO₃ solution are added to residual. The aqueous phase is separated, saturated with K₂CO₃ and extracted with EtOAc. The organic phases are pooled, washed with brine, dried with MgSO₄ and evaporated.

Yield: 351 mg (42%), ESI-MS: m/z=195 (M+H)⁺, $R_t$(HPLC): 0.22 min (HPLC-A)

III. 164 2-piperazin-1-yl-1,3,5-triazine

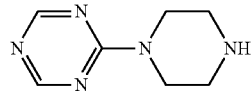 [SMILES: c1ncnc(N2CCNCC2)n1]

A mixture of 38 g (0.216 mol) 1-benzylpiperazine and 25 g (0.145 mol) 2-phenoxy-1,3,5-triazine is heated to 100° C. for 1 h, then cooled to room temperature and diluted with petrol ether. The resulting precipitate was filtered off, washed with petrol ether and recrystallized from EtOH giving rise to 2-(4-benzylpiperazin-1-yl)-1,3,5-triazine Yield: 35 g (95%), mp: 106° C.

A mixture of 25 g (0.1 mol) 2-(4-benzylpiperazin-1-yl)-1,3,5-triazine, 6 g Pd/C and MeOH is stirred under H₂-atmosphere until full conversion is achieved. The solvent is evaporated and petrol ether is added. The resulting precipitate is filtered off and washed with petrol ether.

Yield: 14 g (85%), mp: 67° C., ESI-MS: m/z=166 (M+H)⁺, $R_t$(HPLC): 0.41 min (HPLC-C)

III. 165 5-methyl-2-(1,2,3,6-tetrahydropyridin-4-yl)pyrimidine

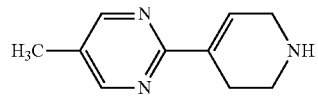

A mixture of 0.5 g (2.89 mmol) 2-bromo-5-methylpyrimidine, 1.1 g (3.47 mmol) tert-butyl 4-(4,4,5,5-tetramethyl-1,3,2-dioxaborolan-2-yl)-3,6-dihydro-2H-pyridine-1-carboxylate, 135 mg (0.12 mmol) tetrakis(triphenylphosphine)palladium(0), 2.9 ml (5.8 mmol) 2M Na₂CO₃ solution and dioxane is heated to 140° C. for 15 min using a microwave reactor. The reaction mixture is cooled to RT and evaporated. DCM and water are added to the residual, the organic phase is separated and evaporated. 15 ml (60 mmol) 4 M HCl in dioxane is added and the mixture was stirred at RT for 2 h. The solvent is evaporated and the crude product purified via FC.

Yield as HCl-salt: 390 mg (62%), ESI-MS: m/z=176 (M+H)⁺

III. 166 5-methoxy-2-(4-piperidyl)pyrimidine

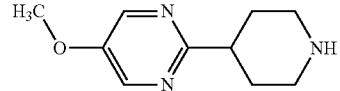

A mixture of 2.1 g (14.5 mmol) 2-chloro-5-methoxypyrimidine, 4.9 g (16.0 mmol) tert-butyl 4-(4,4,5,5-tetramethyl-1,3,2-dioxaborolan-2-yl)-3,6-dihydro-2H-pyridine-1-carboxylate, 339 mg (0.29 mmol) tetrakis(triphenylphosphine)palladium(0), 14.5 ml (29 mmol) 2M Na₂CO₃ solution and dioxane is heated to 140° C. for 15 min using a microwave reactor. The reaction mixture is cooled to RT and DCM and water are added, the organic phase is separated and evaporated and purified by HPLC. Giving rise to tert-butyl 4-(5-methoxypyrimidin-2-yl)-3,6-dihydro-2H-pyridine-1-carboxylate.

Yield: 3.5 g (83%), ESI-MS: m/z=292 (M+H)+

A mixture of 1.8 g (6.18 mmol) tert-butyl 4-(5-methoxy-pyrimidin-2-yl)-3,6-dihydro-2H-pyridine-1-carboxylate, 250 mg Pd/C and MeOH is stirred under H$_2$-atmosphere at 50 psi until full conversion is achieved. The solvent is evaporated and 18 ml (72 mmol) 4 M HCl in dioxane is added and the mixture is stirred at RT for 2 h. The precipitate is filtered off and washed with dioxane.

Yield as HCl-salt: 1.6 g (98%, 85% purity), ESI-MS: m/z=194 (M+H)+

III. 168 3-[4-(cyclopropylmethoxy)phenyl]azetidine

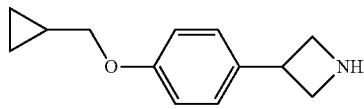

To the mixture of 2.0 g (7.22 mmol) tert-butyl 3-(4-hydroxyphenyl)azetidine-1-carboxylate, 2.1 g (14.44 mmol) K$_2$OC$_3$ and DMF are added 1.17 g (8.66 mmol) bromomethylcyclopropane. The mixture is stirred at 50° C. overnight and then extrated with EtOAc and water. The organic phases are pooled, concentrated and purified by FC. Giving rise to 0.82 g (37%) tert-butyl 3-[4-(cyclopropylmethoxy)phenyl] azetidine-1-carboxylate.

A mixture of 3.00 g (9.49 mmol) tert-butyl 3-[4-(cyclopropylmethoxy)phenyl]azetidine-1-carboxylate, TFA and DCM (55.00 ml) is stirred at 0° C. for 2 h. The pH of the reaction mixture is adjusted to pH 8 with aq. NaHCO$_3$. Then extracted with EtOAc and the organic phase was evaoprated and the residual washed with PE:EtOAc (20:1).

Yield: 1.5 g (78%)

III. 169 methyl 4-(4-piperidyl)piperidine-1-carboxylate

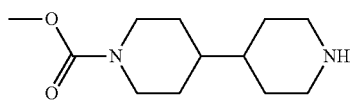

To a mixture of 2.1 g (6.22 mmol) 1-benzyl-4-(4-piperidyl)piperidine dihydrochloride (WO2005/103037), 5.0 ml (28.7 mmol) DIPEA and DCM, 0.6 ml (7.15 mmol) methyl carbonochloridate are added and the mixture is stirred at RT for 15 h. The solvent is evaporated and EtOAc and water are added. The organic phase is separated, dried over Na$_2$SO$_4$ and evaporated.

Yield: 2.0 g (100%), ESI-MS: m/z=317 (M+H)+

A mixture of 2.0 g (6.2 mmol) methyl 4-(1-benzyl-4-piperidyl)piperidine-1-carboxylate, 200 mg Pd/C and MeOH is stirred under H$_2$-atmosphere at 3 bar until full conversion is achieved and the solvent is evaporated.

Yield: 1.4 g (98%), ESI-MS: m/z=227 (M+H)+

The following Intermediates are obtained according to the given references.

| # | Structure/Reference |
|---|---|
| IV.1 | US2014/18368 |
| IV.2 | US2011/152295 |
| IV.3 | WO2009/150240 |
| IV.4 | WO2004/48368 |
| IV.5 | WO2011/25505 |
| IV.6 | US2011/257173 |
| IV.7 | US2013/12530 |
| IV.8 | WO2003/99793 |
| IV.9 | J. Chem. Soc. B, 1970, 1516 |
| IV.10 | US2009/69300 |

| # | Structure/Reference |
|---|---|
| IV.11 | 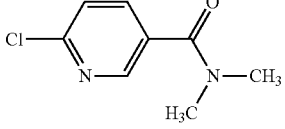<br>WO2006/61193 |

General Procedure 1.A $1^{st}$ step Substition (S): A mixture of 1.0 eq of intermediate I1.02 eq intermediate III, 0.083 eq Xanthphos, 0.02 eq $Pd_2dba_3$ and 1.57 eq $Cs_2CO_3$ in dioxane are heated to the given temperature for the given time. The reaction mixture is purified by HPLC, giving rise to the silyl-protected benzyl alcohol intermediate.

$2^{nd}$ step Deprotection (D): 1.0 eq of the silyl-protected intermediate 3.00 eq of TBAF are stirred at the given temperature for the given time. The reaction mixture is purified by HPLC, giving rise to the alcohol intermediate.

$3^{rd}$ step Acylguanidine formation (A): To a mixture of 1.0 eq of the benzyl alcohol intermediate and DMF 2.2 eq CDI is added and the reaction mixture is stirred at RT overnight. Then 3.5 eq guanidine carbonate are added and the mixture is stirred at RT overnight. The reaction mixture is diluted with MeOH, DMF and acidified with TFA, filtered and purified by HPLC.

General Procedure 1.B $1^{st}$ step Substition (S): A mixture of 1.0 eq of intermediate I1.0 eq intermediate III, 0.15 eq 2-(di-tButylphosphino) biphenyl, 0.10 eq $Pd_2dba_3$ and 3.50 eq $NaO^tBu$ in dioxane are heated to the given temperature for the given time. The reaction mixture is diluted with water and extracted with EtOAc. The oraganic phases are pooled and evaporated. The crude product is purified by FC, giving rise to benzyl alcohol intermediate.

$2^{nd}$ step Acylguanidine formation (A): To a mixture of 1.0 eq of the benzyl alcohol intermediate and DMF 1.5 eq CDI is added and the reaction mixture is stirred at RT for 2 h. Then 2.0 eq guanidine carbonate are added and the mixture is stirred at RT overnight. The reaction mixture is diluted with MeOH, DMF and acidified with TFA, filtered and purified by HPLC.

General Procedure 1. C $1^{st}$ step Substition (S): 1.0 eq of intermediate I 2.0 eq intermediate III and 1.3 eq DIPEA in DMSO are heated to the given temperature for the given time. The resulting the benzyl alcohol intermediate is purified by FC or HPLC.

$2^{nd}$ step Acylguanidine formation (A): To a mixture of 1.0 eq of the benzyl alcohol intermediate and DMF 2.2 eq CDI is added and the reaction mixture is stirred at RT overnight. Then 3.5 eq guanidine carbonate are added and the mixture is stirred at RT overnight. The reaction mixture is diluted with MeOH, DMF and acidified with TFA, filtered and purified by HPLC.

General Procedure 1.D $1^{st}$ step Substition (S): 1.0 eq of intermediate I1.1 eq intermediate III and 1.5 eq DIPEA in DMF are stirred at RT overnight. The reaction mixture is diluted with water and the precipitate is filtered off, giving rise to the ester intermediate.

$2^{nd}$ step Reduction (R): A mixture of 1.0 eq of the ester intermediate, 1 eq 1N NaOH, MeOH and THF (1:1) is stirred for the given time at RT. The reaction mixture is neutralized with 1M HCl, the precipitate is filtered off and dried and then dissolved in THF. 1.1 eq CDI are added and the mixture is stirred at 50° C. for 2 h. This mixture is slowly added to a solution of 3.0 eq $NaBH_4$ in water at 0° C., than allowed to warm to RT and stirred for 1.5 h. The reaction mixture is carefully acidified with 4M HCl and stirred for 30 min, then basified with $NH_4OH$, diluted with water and extracted with EtOAc. The organic phase is dried and evaporated and the residual purified by FC, furnishing the benzyl alcohol intermediate.

$3^{rd}$ step Acylguanidine formation (A): Is carried out as described in General Procedure 1.B.

General Procedure 1.E $1^{st}$ step Substition (S): Is carried out as described in General Procedure 1.C. $2^{nd}$ step Acylguanidine formation (A): To a mixture of 1.0 eq of the benzyl alcohol intermediate and DMF 2.0 eq CDI is added and the reaction mixture is stirred at RT for 8 h. Then 3.0 eq guanidine carbonate are added and the mixture is stirred at RT overnight. The reaction mixture is diluted with ACN and water and purified by HPLC.

General Procedure 1.F $1^{st}$ step Substition (S): 1.0 eq of intermediate I1.75 eq intermediate IV and 3.0 eq DIPEA in DMSO are heated to the given temperature for the given time. The resulting the benzyl alcohol intermediate is purified by FC or HPLC.

$2^{nd}$ step Acylguanidine formation (A): Is carried out as described in General Procedure 1.E.

The following examples in table 2 (example number given in column #) are prepared according to general procedure 1.A-1F, details are given in the column synthesis comment, the retention-time and mass (ESI-MS m/z M+H$^+$) determined by HPLC-MS are given in the columns MS and RT.

TABLE 2

| # | Structure | I/II | III/IV | MS | RT | Synthesis Comment |
|---|---|---|---|---|---|---|
| 1.001 | 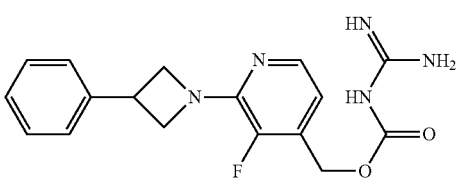 [SMILES: N=C(N)NC(=O)OCc1ccnc(N2CC(c3ccccc3)C2)c1F] | I.1 | III.54 | 344 | 0.64 min HPLC-G | S: 100° C., overnight |

TABLE 2-continued

| # | Structure | I/II | III/IV | MS | RT | Synthesis Comment |
|---|---|---|---|---|---|---|
| 1.002 | 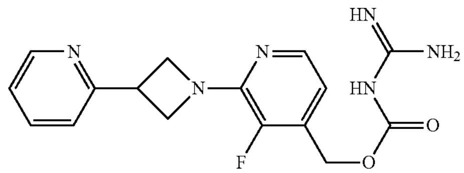 [SMILES: N=C(N)NC(=O)OCc1ccnc(N2CC(c3ccccn3)C2)c1F] | I.1 | III.74 | 345 | 0.48 min HPLC-G | S: 100° C., overnight |
| 1.003 | 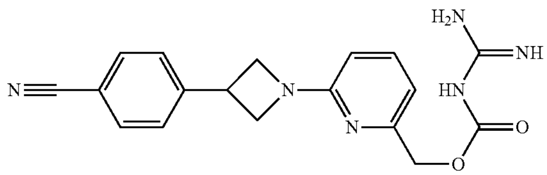 [SMILES: N#Cc1ccc(C2CN(c3cccc(COC(=O)NC(=N)N)n3)C2)cc1] | I.60 | III.16 | 351 | 0.68 min HPLC-A | S: 100° C., 2 h |
| 1.004 | 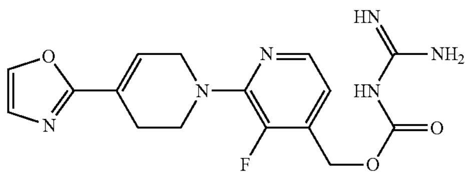 | I.1 | III.67 | 361 | 0.51 min HPLC-G | S: 100° C., overnight |
| 1.005 | 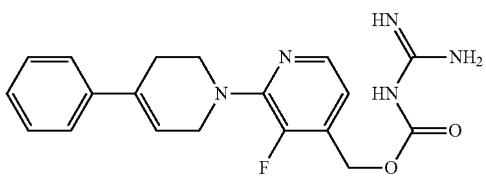 [SMILES: N=C(N)NC(=O)OCc1ccnc(N2CC=C(c3ccccc3)CC2)c1F] | I.1 | III.35 | 370 | 0.74 min HPLC-G | S: 100° C., overnight |
| 1.006 | 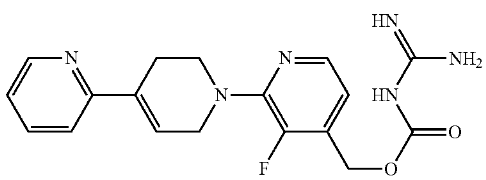 [SMILES: N=C(N)NC(=O)OCc1ccnc(N2CC=C(c3ccccn3)CC2)c1F] | I.1 | III.9 | 371 | 0.57 min HPLC-G | S: 100° C., overnight |
| 1.007 | 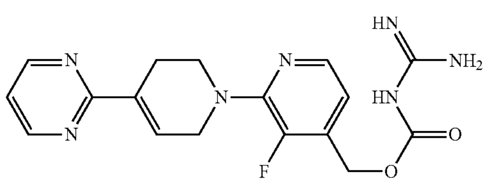 | I.1 | III.70 | 372 | 0.51 min HPLC-G | S: 100° C., overnight |
| 1.008 | 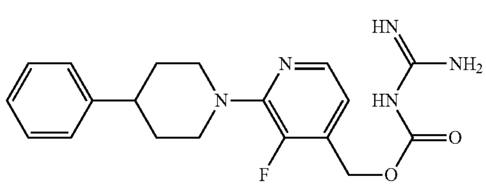 [SMILES: N=C(N)NC(=O)OCc1ccnc(N2CCC(c3ccccc3)CC2)c1F] | I.1 | III.80 | 372 | 0.75 min HPLC-G | S: 100° C., overnight |
| 1.009 | 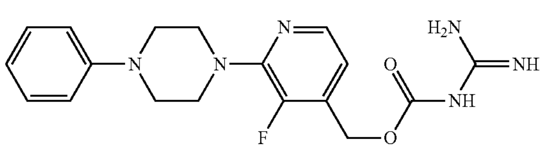 [SMILES: N=C(N)NC(=O)OCc1ccnc(N2CCN(c3ccccc3)CC2)c1F] | I.1 | III.12 | 373 | 0.66 min HPLC-G | S: 100° C., overnight |

TABLE 2-continued

| # | Structure | I/II | III/IV | MS | RT | Synthesis Comment |
|---|---|---|---|---|---|---|
| 1.010 | 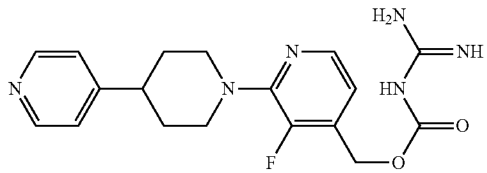 [SMILES: N=C(N)NC(=O)OCc1ccnc(N2CCC(c3ccncc3)CC2)c1F] | I.1 | III.2 | 373 | 0.8 min HPLC-C | S: 100° C., overnight |
| 1.011 | 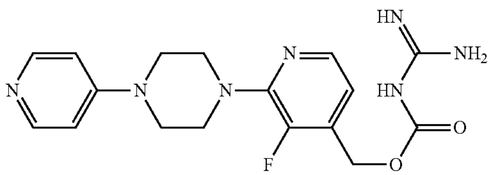 [SMILES: N=C(N)NC(=O)OCc1ccnc(N2CCN(c3ccncc3)CC2)c1F] | I.1 | III.8 | 374 | 0.47 min HPLC-G | S: 100° C., overnight |
| 1.012 | 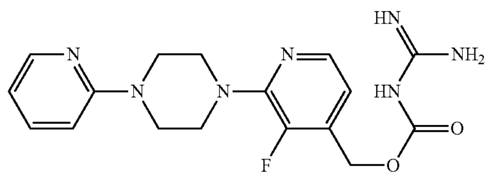 | I.1 | III.81 | 374 | 0.57 min HPLC-G | S: 100° C., overnight |
| 1.013 | 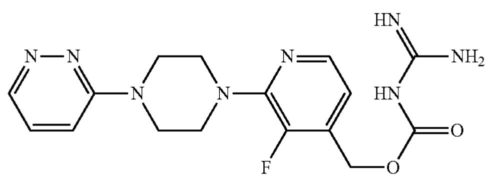 | I.1 | III.60 | 375 | 0.42 min HPLC-G | S: 100° C., overnight |
| 1.014 | 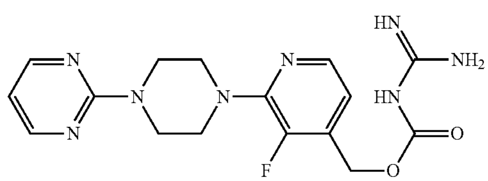 | I.1 | III.82 | 375 | 0.53 min HPLC-G | S: 100° C., overnight |
| 1.015 | 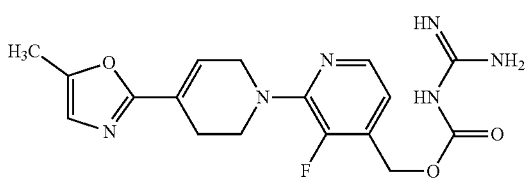 | I.1 | III.68 | 375 | 0.57 min HPLC-G | S: 100° C., overnight |
| 1.016 | 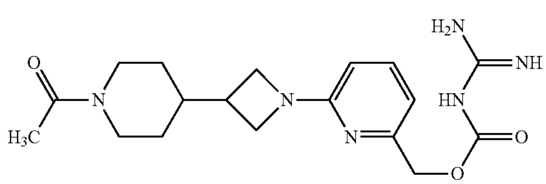 [SMILES: CC(=O)N1CCC(C2CN(c3cccc(COC(=O)NC(=N)N)n3)C2)CC1] | I.60 | III.162 | 375 | 0.6 min HPLC-A | S: 80° C., 1 h |
| 1.017 | 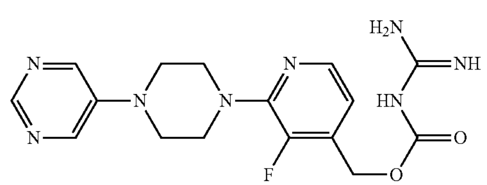 [SMILES: N=C(N)NC(=O)OCc1ccnc(N2CCN(c3cncnc3)CC2)c1F] | I.1 | III.1 | 375 | 0.65 min HPLC-A | S: 100° C., overnight |

TABLE 2-continued

| # | Structure | I/II | III/IV | MS | RT | Synthesis Comment |
|---|---|---|---|---|---|---|
| 1.018 | 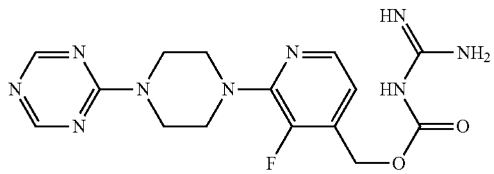 [SMILES: N=C(N)NC(=O)OCc1ccnc(N2CCN(c3ncncn3)CC2)c1F] | I.1 | III.164 | 376 | 0.45 min HPLC-G | S: 100° C., overnight |
| 1.019 | 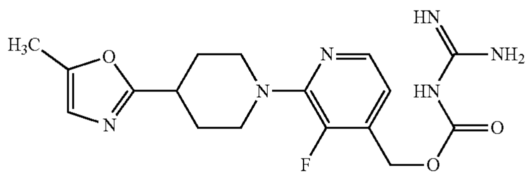 | I.1 | III.20 | 377 | 0.55 min HPLC-G | S: 100° C., overnight |
| 1.020 | 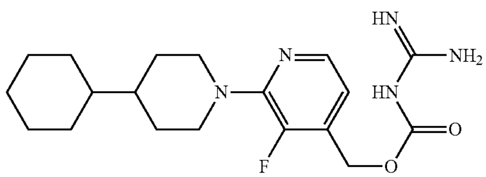 [SMILES: N=C(N)NC(=O)OCc1ccnc(N2CCC(C3CCCCC3)CC2)c1F] | I.1 | III.6 | 378 | 0.94 min HPLC-G | S: 100° C., overnight |
| 1.021 | 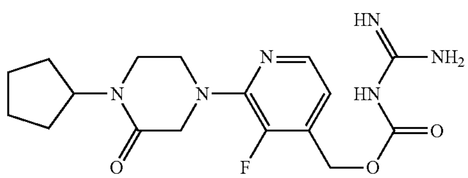 [SMILES: N=C(N)NC(=O)OCc1ccnc(N2CCN(C3CCCC3)C(=O)C2)c1F] | I.1 | III.61 | 379 | 0.52 min HPLC-G | S: 100° C., overnight |
| 1.022 | 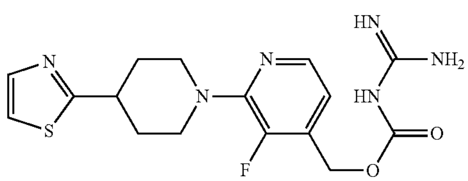 [SMILES: N=C(N)NC(=O)OCc1ccnc(N2CCC(c3nccs3)CC2)c1F] | I.1 | III.57 | 379 | 0.55 min HPLC-G | S: 100° C., overnight |
| 1.023 | 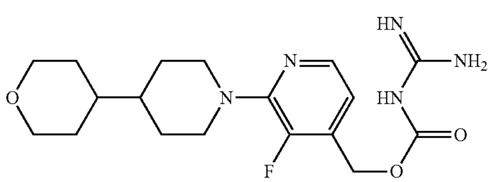 [SMILES: N=C(N)NC(=O)OCc1ccnc(N2CCC(C3CCOCC3)CC2)c1F] | I.1 | III.56 | 380 | 0.6 min HPLC-G | S: 100° C., overnight |
| 1.024 | 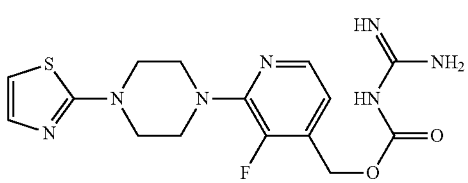 [SMILES: N=C(N)NC(=O)OCc1ccnc(N2CCN(c3nccs3)CC2)c1F] | I.1 | III.30 | 380 | 0.54 min HPLC-G | S: 100° C., overnight |
| 1.025 | 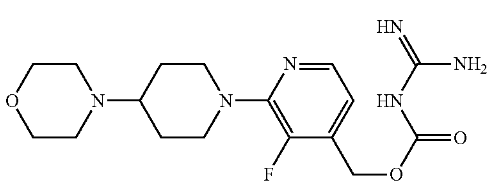 | I.1 | III.4 | 381 | 0.44 min HPLC-G | S: 100° C., overnight |

TABLE 2-continued

| # | Structure | I/II | III/IV | MS | RT | Synthesis Comment |
|---|---|---|---|---|---|---|
| 1.026 | 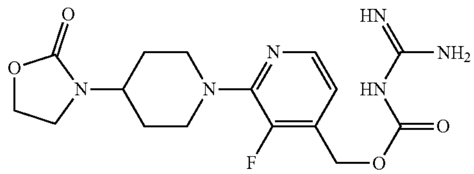 [SMILES: N=C(N)NC(=O)OCc1ccnc(N2CCC(N3CCOC3=O)CC2)c1F] | I.1 | III.69 | 381 | 0.41 min HPLC-G | S: 100° C., overnight |
| 1.027 | 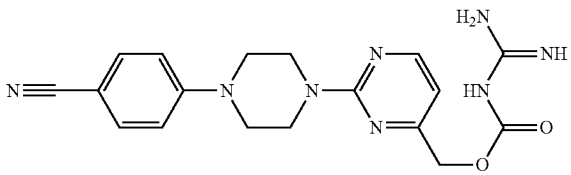 [SMILES: N#Cc1ccc(N2CCN(c3nccc(COC(=O)NC(=N)N)n3)CC2)cc1] | I.61 | III.14 | 381 | 0.79 min HPLC-A | R: 1 h |
| 1.028 | 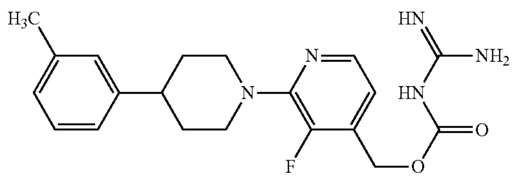 | I.1 | III.55 | 386 | 0.8 min HPLC-G | S: 100° C., overnight |
| 1.029 | 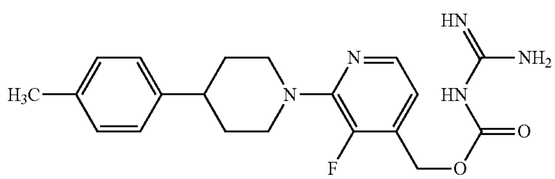 [SMILES: Cc1ccc(C2CCN(c3nccc(COC(=O)NC(=N)N)c3F)CC2)cc1] | I.1 | III.49 | 386 | 0.8 min HPLC-G | S: 100° C., overnight |
| 1.030 | 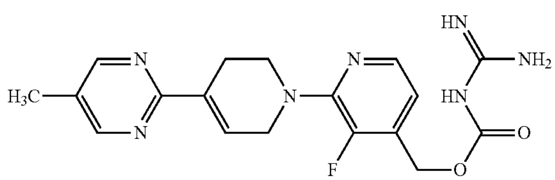 [SMILES: Cc1cnc(C2=CCN(c3nccc(COC(=O)NC(=N)N)c3F)CC2)nc1] | I.1 | III.165 | 386 | 0.56 min HPLC-G | S: 100° C., overnight |
| 1.031 | 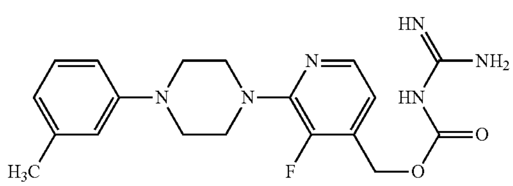 [SMILES: Cc1cccc(N2CCN(c3nccc(COC(=O)NC(=N)N)c3F)CC2)c1] | I.1 | III.84 | 387 | 0.72 min HPLC-G | S: 100° C., overnight |
| 1.032 | 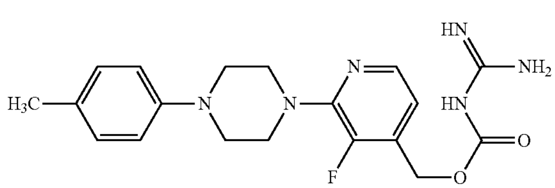 [SMILES: Cc1ccc(N2CCN(c3nccc(COC(=O)NC(=N)N)c3F)CC2)cc1] | I.1 | III.86 | 387 | 0.72 min HPLC-G | S: 100° C., overnight |
| 1.033 | 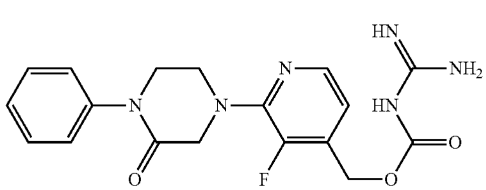 [SMILES: N=C(N)NC(=O)OCc1ccnc(N2CCN(c3ccccc3)C(=O)C2)c1F] | I.1 | III.44 | 387 | 0.5 min HPLC-G | S: 100° C., overnight |

TABLE 2-continued

| # | Structure | I/II | III/IV | MS | RT | Synthesis Comment |
|---|---|---|---|---|---|---|
| 1.034 | 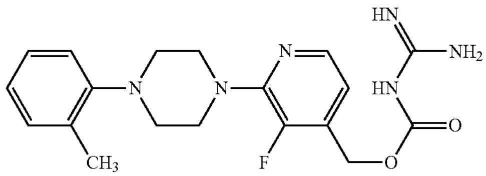 [SMILES: Cc1ccccc1N1CCN(c2nccc(COC(=O)NC(=N)N)c2F)CC1] | I.1 | III.27 | 387 | 0.77 min HPLC-G | S: 100° C., overnight |
| 1.035 | 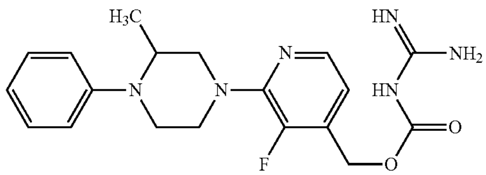 [SMILES: CC1CN(c2nccc(COC(=O)NC(=N)N)c2F)CCN1c1ccccc1] | I.1 | III.32 | 387 | 0.72 min HPLC-G | S: 100° C., overnight |
| 1.036 | 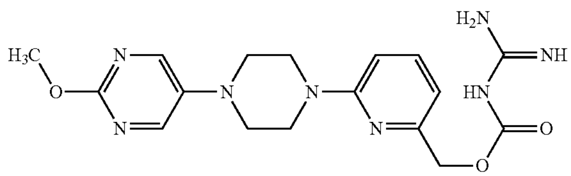 | I.60 | III.163 | 387 | 0.67 min HPLC-A | S: 100° C., 2 h |
| 1.037 | 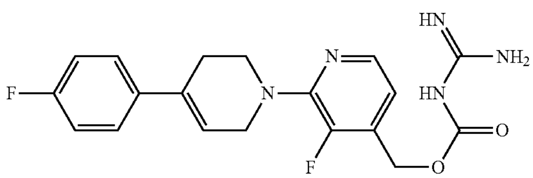 [SMILES: N=C(N)NC(=O)OCc1ccnc(N2CC=C(c3ccc(F)cc3)CC2)c1F] | I.1 | III.31 | 388 | 0.75 min HPLC-G | S: 100° C., overnight |
| 1.038 | 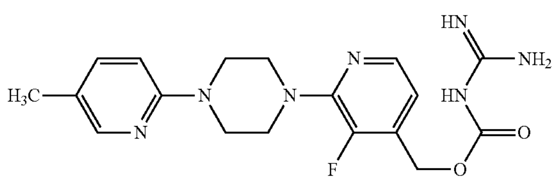 [SMILES: Cc1ccc(N2CCN(c3nccc(COC(=O)NC(=N)N)c3F)CC2)nc1] | I.1 | III.59 | 388 | 0.62 min HPLC-G | S: 100° C., overnight |
| 1.039 | 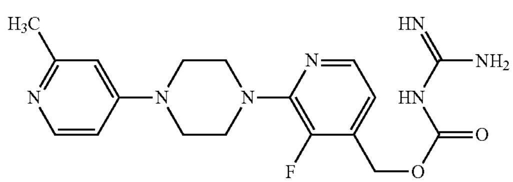 [SMILES: Cc1cc(N2CCN(c3nccc(COC(=O)NC(=N)N)c3F)CC2)ccn1] | I.1 | III.19 | 388 | 0.5 min HPLC-G | S: 100° C., overnight |
| 1.040 | 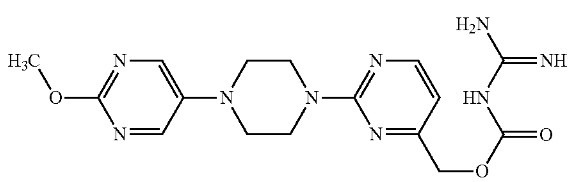 [SMILES: COc1ncc(N2CCN(c3nccc(COC(=O)NC(=N)N)n3)CC2)cn1] | I.61 | III.163 | 388 | 0.7 min HPLC-A | R: 2 h |
| 1.041 | 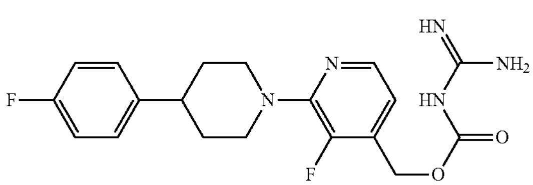 [SMILES: N=C(N)NC(=O)OCc1ccnc(N2CCC(c3ccc(F)cc3)CC2)c1F] | I.1 | III.53 | 390 | 0.75 min HPLC-G | S: 100° C., overnight |

TABLE 2-continued

| # | Structure | I/II | III/IV | MS | RT | Synthesis Comment |
|---|---|---|---|---|---|---|
| 1.042 | 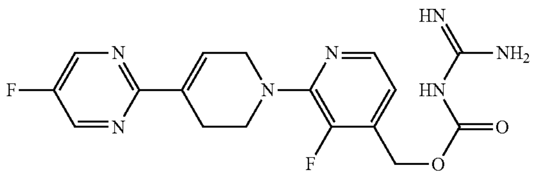 [SMILES: N=C(N)NC(=O)OCc1ccnc(N2CC=C(c3ncc(F)cn3)CC2)c1F] | I.1 | III.160 | 390 | 0.59 min HPLC-G | S: 100° C., overnight |
| 1.043 | 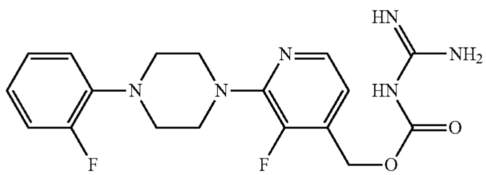 [SMILES: N=C(N)NC(=O)OCc1ccnc(N2CCN(c3ccccc3F)CC2)c1F] | I.1 | III.36 | 391 | 0.7 min HPLC-G | S: 100° C., overnight |
| 1.044 | 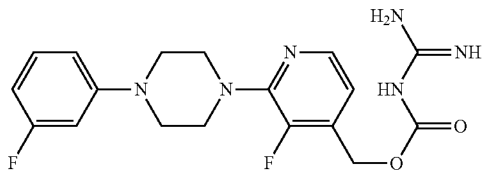 [SMILES: N=C(N)NC(=O)OCc1ccnc(N2CCN(c3cccc(F)c3)CC2)c1F] | I.1 | III.40 | 391 | 0.96 min HPLC-C | S: 100° C., overnight |
| 1.045 | 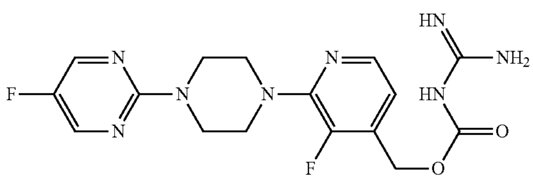 [SMILES: N=C(N)NC(=O)OCc1ccnc(N2CCN(c3ncc(F)cn3)CC2)c1F] | I.1 | III.78 | 393 | 0.61 min HPLC-G | S: 100° C., overnight |
| 1.046 | 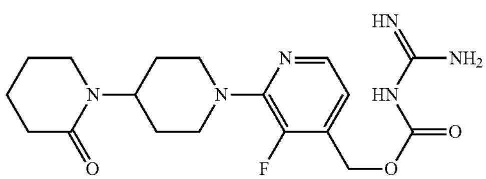 [SMILES: N=C(N)NC(=O)OCc1ccnc(N2CCC(N3CCCCC3=O)CC2)c1F] | I.1 | III.7 | 393 | 0.47 min HPLC-G | S: 100° C., overnight |
| 1.047 | 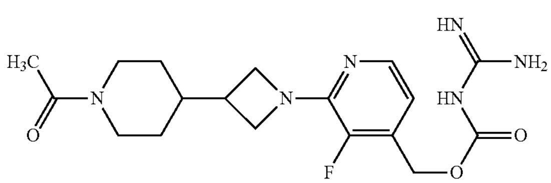 [SMILES: CC(=O)N1CCC(C2CN(c3nccc(COC(=O)NC(=N)N)c3F)C2)CC1] | I.1 | III.162 | 393 | 0.61 min HPLC-A | S: 100° C., overnight |
| 1.048 | 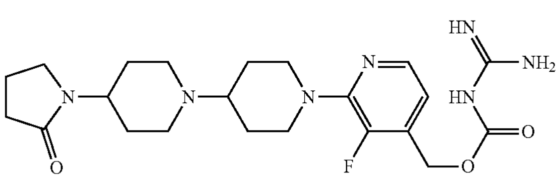 [SMILES: N=C(N)NC(=O)OCc1ccnc(N2CCC(N3CCC(N4CCCC4=O)CC3)CC2)c1F] | I.1 | III.18 | 395 | 0.43 min HPLC-G | S: 100° C., overnight |
| 1.049 | 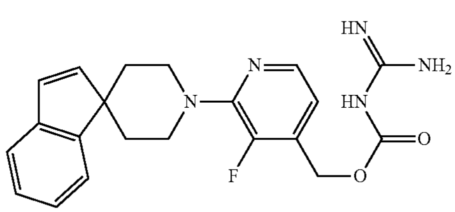 [SMILES: N=C(N)NC(=O)OCc1ccnc(N2CCC3(C=Cc4ccccc43)CC2)c1F] | I.1 | III.52 | 396 | 0.78 min HPLC-G | S: 100° C., overnight |

TABLE 2-continued

| # | Structure | I/II | III/IV | MS | RT | Synthesis Comment |
|---|---|---|---|---|---|---|
| 1.050 | 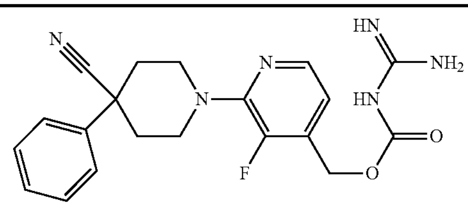 | I.1 | III.3 | 397 | 0.67 min HPLC-G | S: 100° C., overnight |
| 1.051 | 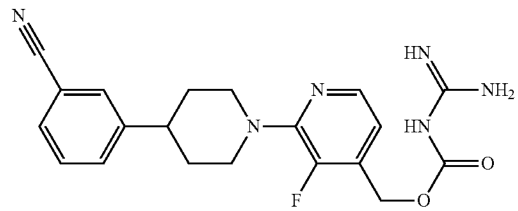 [SMILES: N#Cc1cccc(C2CCN(c3nccc(COC(=O)NC(=N)N)c3F)CC2)c1] | I.1 | III.21 | 397 | 0.67 min HPLC-G | S: 100° C., overnight |
| 1.052 | 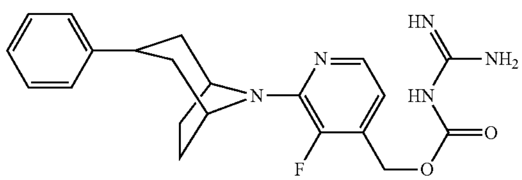 [SMILES: N=C(N)NC(=O)OCc1ccnc(N2C3CCC2CC(c2ccccc2)C3)c1F] | I.1 | III.65 | 398 | 0.8 min HPLC-G | S: 100° C., overnight |
| 1.053 | 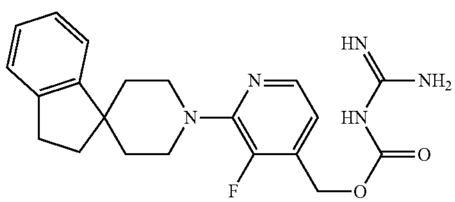 [SMILES: N=C(N)NC(=O)OCc1ccnc(N2CCC3(CCc4ccccc43)CC2)c1F] | I.1 | III.25 | 398 | 0.8 min HPLC-G | S: 100° C., overnight |
| 1.054 | 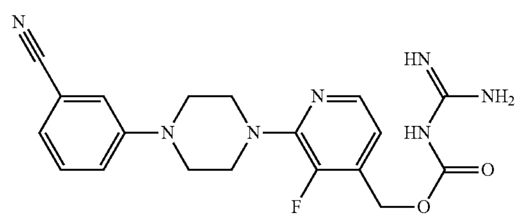 [SMILES: N#Cc1cccc(N2CCN(c3nccc(COC(=O)NC(=N)N)c3F)CC2)c1] | I.1 | III.43 | 398 | 0.64 min HPLC-G | S: 100° C., overnight |
| 1.055 | 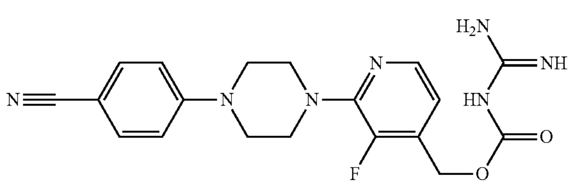 [SMILES: N#Cc1ccc(N2CCN(c3nccc(COC(=O)NC(=N)N)c3F)CC2)cc1] | I.1 | III.14 | 398 | 0.8 min HPLC-A | S: 80° C., overnight |
| 1.056 | 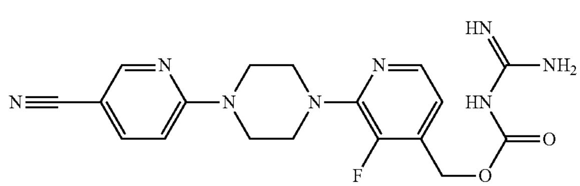 [SMILES: N#Cc1ccc(N2CCN(c3nccc(COC(=O)NC(=N)N)c3F)CC2)nc1] | I.1 | III.46 | 399 | 0.57 min HPLC-G | S: 100° C., overnight |
| 1.057 | 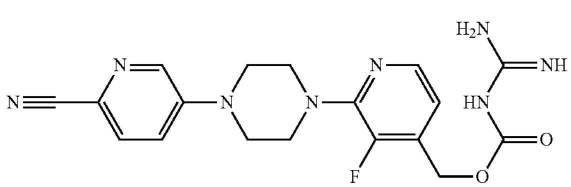 [SMILES: N#Cc1ccc(N2CCN(c3nccc(COC(=O)NC(=N)N)c3F)CC2)cn1] | II.1 | IV.9 | 399 | 0.78 min HPLC-A | S: 80° C., overnight |

TABLE 2-continued
| # | Structure | I/II | III/IV | MS | RT | Synthesis Comment |
|---|---|---|---|---|---|---|
| 1.058 | 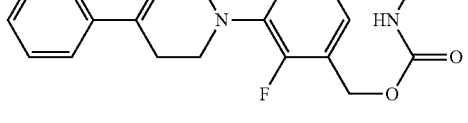 | I.1 | III.63 | 400 | 0.72 min HPLC-G | S: 100° C., overnight |
| 1.059 | 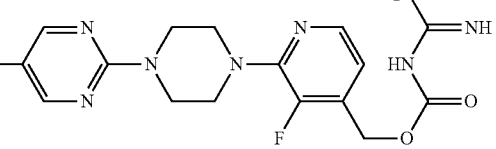 | II.1 | IV.2 | 400 | 0.8 min HPLC-A | S: 80° C., overnight |
| 1.060 | 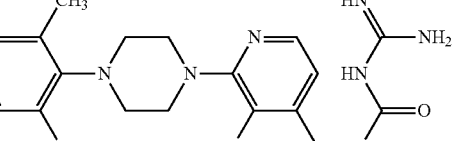 | I.1 | III.17 | 401 | 0.84 min HPLC-G | S: 100° C., overnight |
| 1.061 | 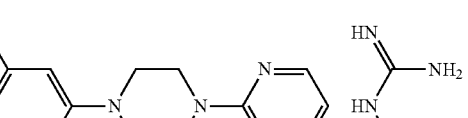 | I.1 | III.37 | 401 | 0.79 min HPLC-G | S: 100° C., overnight |
| 1.062 | 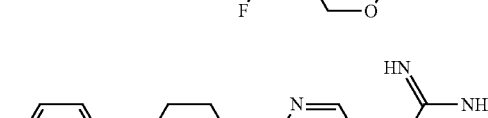 | I.1 | III.34 | 401 | 0.78 min HPLC-G | S: 100° C., overnight |
| 1.063 | 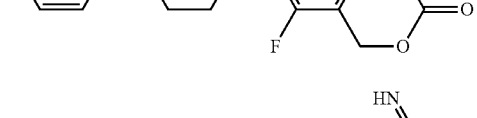 | I.1 | III.87 | 401 | 0.77 min HPLC-G | S: 100° C., overnight |
| 1.064 | 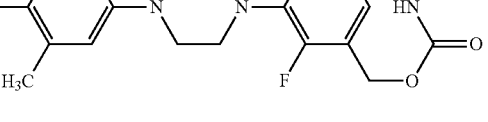 | I.1 | III.71 | 402 | 0.56 min HPLC-G | S: 100° C., overnight |
| 1.065 | 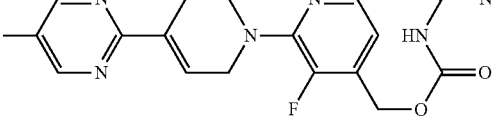 | I.1 | III.41 | 402 | 0.73 min HPLC-G | S: 100° C., overnight |

TABLE 2-continued
| # | Structure | I/II | III/IV | MS | RT | Synthesis Comment |
|---|---|---|---|---|---|---|
| 1.066 | 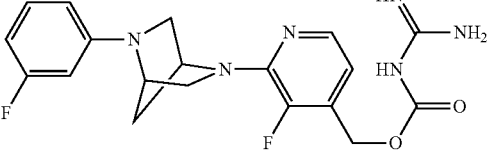 | I.1 | III.15 | 403 | 0.69 min HPLC-G | S: 100° C., overnight |
| 1.067 | 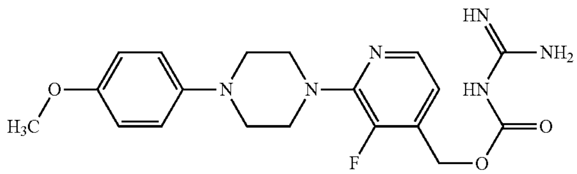 [SMILES: COc1ccc(N2CCN(c3nccc(COC(=O)NC(=N)N)c3F)CC2)cc1] | I.1 | III.83 | 403 | 0.63 min HPLC-G | S: 100° C., overnight |
| 1.068 | 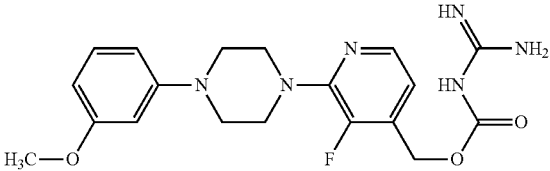 [SMILES: COc1cccc(N2CCN(c3nccc(COC(=O)NC(=N)N)c3F)CC2)c1] | I.1 | III.22 | 403 | 0.66 min HPLC-G | S: 100° C., overnight |
| 1.069 | 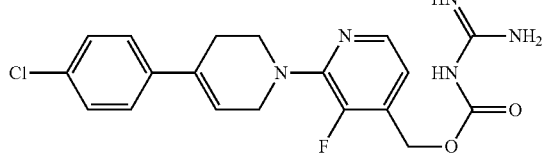 | I.1 | III.85 | 404 | 0.82 min HPLC-G | S: 100° C., overnight |
| 1.070 | 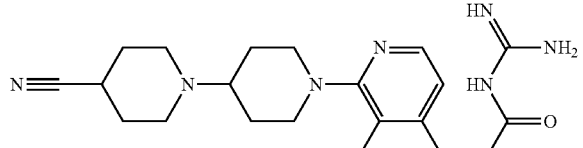 | I.1 | III.11 | 404 | 0.5 min HPLC-G | S: 100° C., overnight |
| 1.071 | 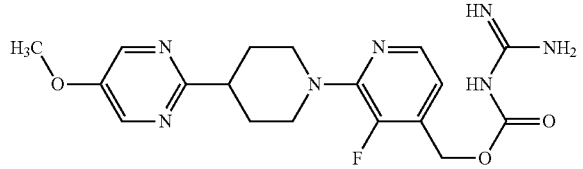 [SMILES: COc1cnc(C2CCN(c3nccc(COC(=O)NC(=N)N)c3F)CC2)nc1] | I.1 | III.166 | 404 | 0.52 min HPLC-G | S: 100° C., overnight |
| 1.072 | 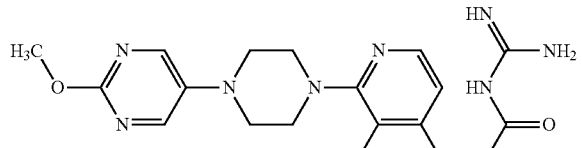 | I.3 | III.163 | 405 | 0.71 min HPLC-A | S: 100° C., overnight D: 0° C., 1 h |
| 1.073 | 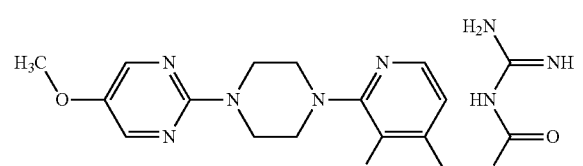 | I.1 | III.77 | 405 | 0.74 min HPLC-A | S: 100° C., 48 h |

TABLE 2-continued
| # | Structure | I/II | III/IV | MS | RT | Synthesis Comment |
|---|---|---|---|---|---|---|
| 1.074 | 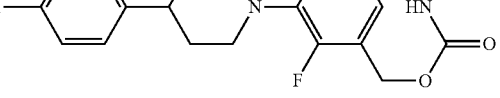 | I.1 | III.50 | 406 | 0.81 min HPLC-G | S: 100° C., overnight |
| 1.075 | 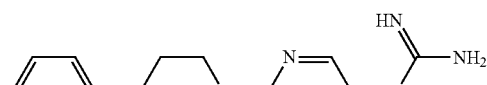 | I.1 | III.48 | 406 | 0.81 min HPLC-G | S: 100° C., overnight |
| 1.076 | 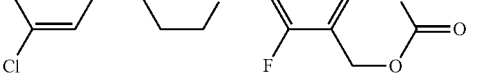 | I.1 | III.29 | 407 | 0.76 min HPLC-G | S: 100° C., overnight |
| 1.077 | 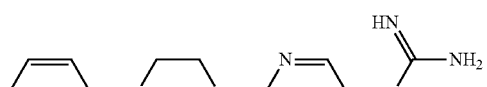 | I.1 | III.5 | 407 | 0.76 min HPLC-G | S: 100° C., overnight |
| 1.078 | 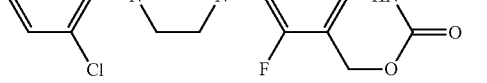 | I.1 | III.47 | 408 | 0.69 min HPLC-G | S: 100° C., overnight |
| 1.079 | 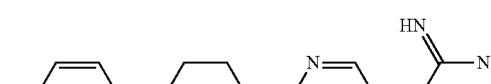 | I.1 | III.62 | 408 | 0.61 min HPLC-G | S: 100° C., overnight |
| 1.080 | 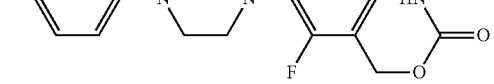 | I.1 | III.10 | 413 | 0.35 min HPLC-G | S: 100° C., overnight |
| 1.081 | 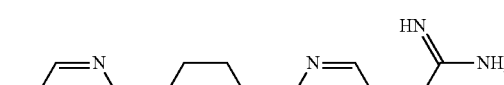 | I.1 | III.168 | 414 | 0.74 min HPLC-G | S: 100° C., overnight |

TABLE 2-continued

| # | Structure | I/II | III/IV | MS | RT | Synthesis Comment |
|---|---|---|---|---|---|---|
| 1.082 | 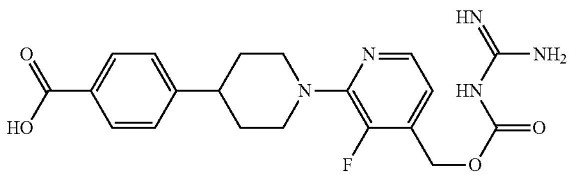 [SMILES: N=C(N)NC(=O)OCc1ccnc(N2CCC(c3ccc(C(=O)O)cc3)CC2)c1F] | I.1 | III.42 | 414 | 0.51 min HPLC-G | S: 100° C., overnight |
| 1.083 | 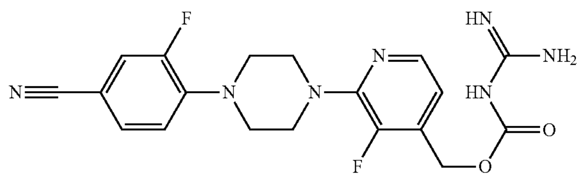 [SMILES: N#Cc1ccc(N2CCN(c3nccc(COC(=O)NC(=N)N)c3F)CC2)c(F)c1] | I.1 | III.73 | 416 | 0.65 min HPLC-G | S: 100° C., overnight |
| 1.084 | 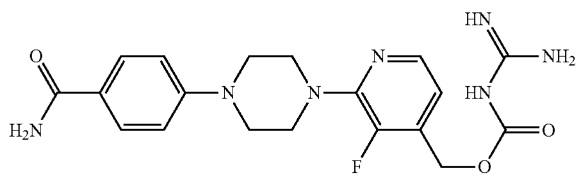 [SMILES: N=C(N)NC(=O)OCc1ccnc(N2CCN(c3ccc(C(N)=O)cc3)CC2)c1F] | I.1 | III.39 | 416 | 0.44 min HPLC-G | S: 100° C., overnight |
| 1.085 | 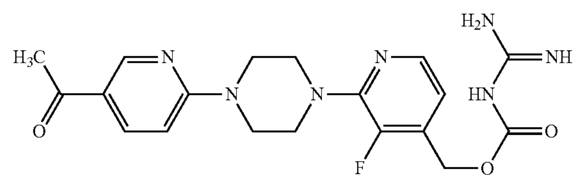 [SMILES: CC(=O)c1ccc(N2CCN(c3nccc(COC(=O)NC(=N)N)c3F)CC2)nc1] | II.1 | IV.7 | 416 | 0.71 min HPLC-A | S: 80° C., overnight |
| 1.086 | 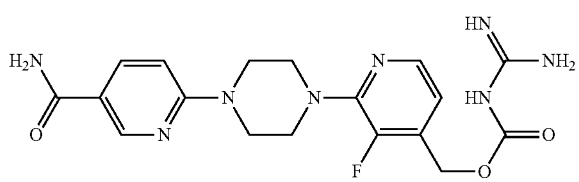 [SMILES: N=C(N)NC(=O)OCc1ccnc(N2CCN(c3ccc(C(N)=O)cn3)CC2)c1F] | I.1 | III.24 | 417 | 0.42 min HPLC-G | S: 100° C., overnight |
| 1.087 | 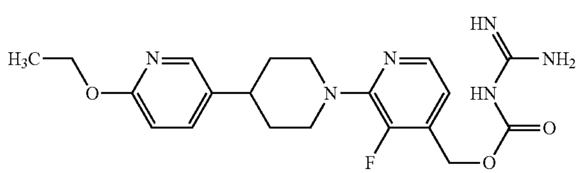 [SMILES: CCOc1ccc(C2CCN(c3nccc(COC(=O)NC(=N)N)c3F)CC2)cn1] | I.1 | III.76 | 417 | 0.69 min HPLC-G | S: 100° C., overnight |
| 1.088 | 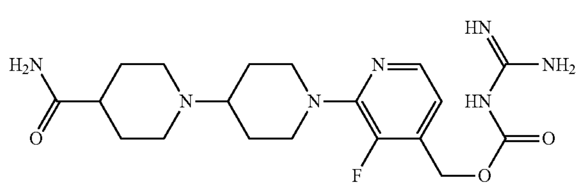 [SMILES: N=C(N)NC(=O)OCc1ccnc(N2CCC(N3CCC(C(N)=O)CC3)CC2)c1F] | I.1 | III.26 | 422 | 0.39 min HPLC-G | S: 100° C., overnight |
| 1.089 | 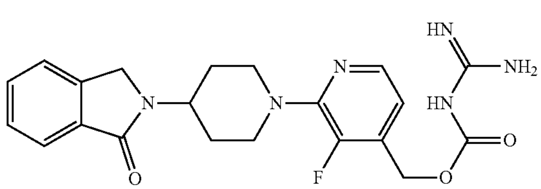 [SMILES: N=C(N)NC(=O)OCc1ccnc(N2CCC(N3Cc4ccccc4C3=O)CC2)c1F] | I.1 | III.13 | 427 | 0.54 min HPLC-G | S: 100° C., overnight |

TABLE 2-continued

| # | Structure | I/II | III/IV | MS | RT | Synthesis Comment |
|---|---|---|---|---|---|---|
| 1.090 | 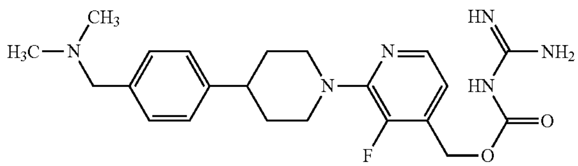 [SMILES: CN(C)Cc1ccc(C2CCN(c3nccc(COC(=O)NC(=N)N)c3F)CC2)cc1] | I.1 | III.33 | 429 | 0.7 min HPLC-G | S: 100° C., overnight |
| 1.091 | 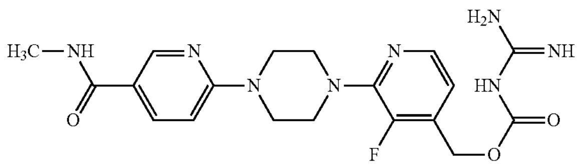 [SMILES: CNC(=O)c1ccc(N2CCN(c3nccc(COC(=O)NC(=N)N)c3F)CC2)nc1] | II.1 | IV.10 | 431 | 0.77 min HPLC-C | S: 80° C., overnight |
| 1.092 | 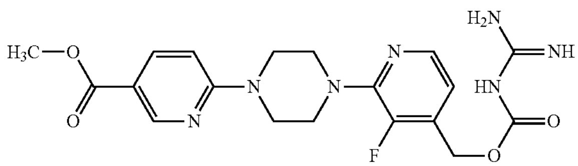 [SMILES: COC(=O)c1ccc(N2CCN(c3nccc(COC(=O)NC(=N)N)c3F)CC2)nc1] | II.1 | IV.5 | 432 | 0.75 min HPLC-A | S: 80° C., overnight |
| 1.093 | 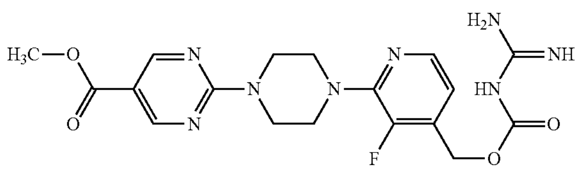 [SMILES: COC(=O)c1cnc(N2CCN(c3nccc(COC(=O)NC(=N)N)c3F)CC2)nc1] | II.1 | IV.1 | 433 | 0.82 min HPLC-A | S: 80° C., overnight |
| 1.094 | 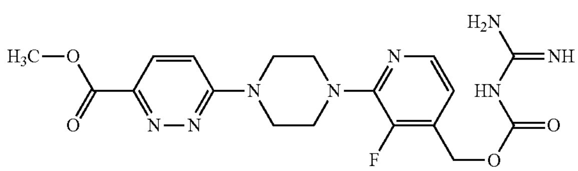 [SMILES: COC(=O)c1ccc(N2CCN(c3nccc(COC(=O)NC(=N)N)c3F)CC2)nn1] | II.1 | IV.6 | 433 | 0.72 min HPLC-A | S: 80° C., overnight |
| 1.095 | 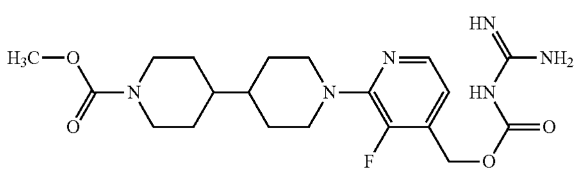 [SMILES: COC(=O)N1CCC(C2CCN(c3nccc(COC(=O)NC(=N)N)c3F)CC2)CC1] | I.1 | III.169 | 437 | 0.64 min HPLC-G | S: 100° C., overnight |
| 1.096 | 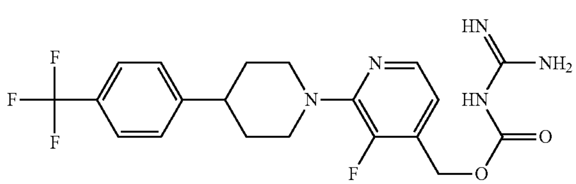 [SMILES: N=C(N)NC(=O)OCc1ccnc(N2CCC(c3ccc(C(F)(F)F)cc3)CC2)c1F] | I.1 | III.45 | 440 | 0.83 min HPLC-G | S: 100° C., overnight |
| 1.097 | 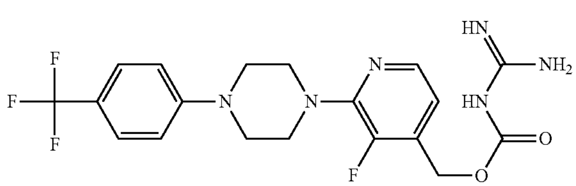 [SMILES: N=C(N)NC(=O)OCc1ccnc(N2CCN(c3ccc(C(F)(F)F)cc3)CC2)c1F] | I.1 | III.38 | 441 | 0.79 min HPLC-G | S: 100° C., overnight |
| 1.098 | 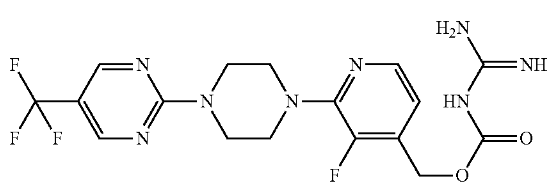 [SMILES: N=C(N)NC(=O)OCc1ccnc(N2CCN(c3ncc(C(F)(F)F)cn3)CC2)c1F] | II.1 | IV.3 | 443 | 0.91 min HPLC-A | S: 80° C., overnight |

TABLE 2-continued

| # | Structure | I/II | III/IV | MS | RT | Synthesis Comment |
|---|---|---|---|---|---|---|
| 1.099 | 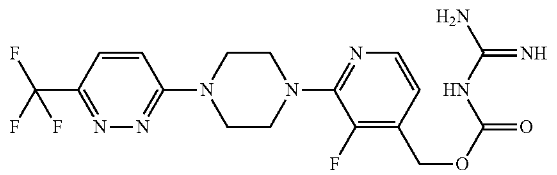 [SMILES: N=C(N)NC(=O)OCc1ccnc(N2CCN(c3ccc(C(F)(F)F)nn3)CC2)c1F] | II.1 | IV.8 | 443 | 0.82 min HPLC-A | S: 80° C., overnight |
| 1.100 | 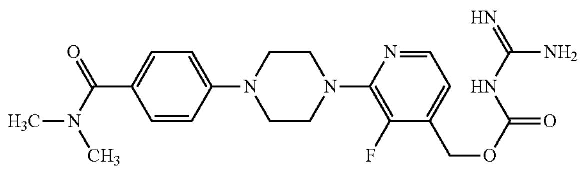 [SMILES: CN(C)C(=O)c1ccc(N2CCN(c3nccc(COC(=O)NC(=N)N)c3F)CC2)cc1] | I.1 | III.51 | 444 | 0.52 min HPLC-G | S: 100° C., overnight |
| 1.101 | 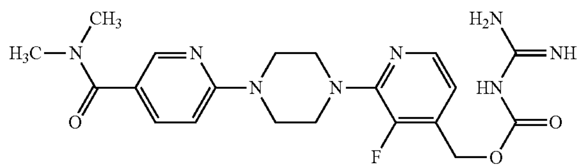 [SMILES: CN(C)C(=O)c1ccc(N2CCN(c3nccc(COC(=O)NC(=N)N)c3F)CC2)nc1] | II.1 | IV.11 | 445 | 0.81 min HPLC-C | S: 80° C., overnight |
| 1.102 | 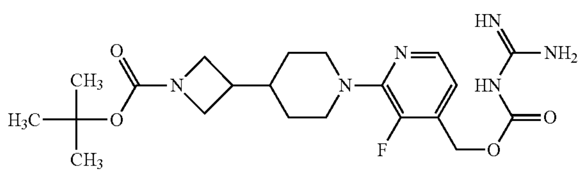 | I.1 | III.28 | 451 | 0.71 min HPLC-G | S: 100° C., overnight |
| 1.103 | 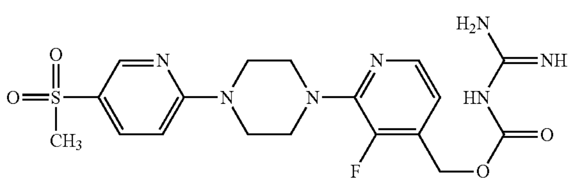 [SMILES: CS(=O)(=O)c1ccc(N2CCN(c3nccc(COC(=O)NC(=N)N)c3F)CC2)nc1] | II.1 | IV.4 | 452 | 0.74 min HPLC-A | S: 80° C., overnight |
| 1.104 | 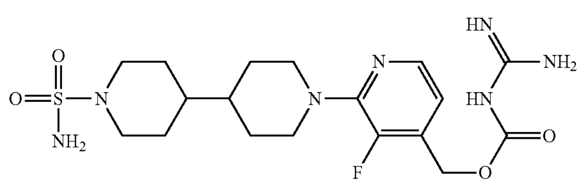 [SMILES: N=C(N)NC(=O)OCc1ccnc(N2CCC(C3CCN(S(N)(=O)=O)CC3)CC2)c1F] | I.1 | III.66 | 458 | 0.5 min HPLC-G | S: 100° C., overnight |
| 1.105 | 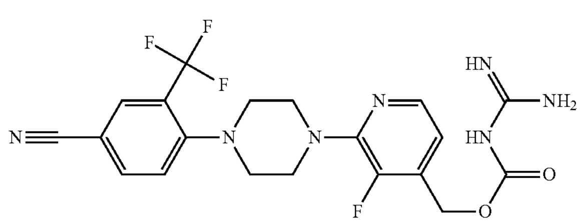 [SMILES: N#Cc1ccc(N2CCN(c3nccc(COC(=O)NC(=N)N)c3F)CC2)c(C(F)(F)F)c1] | I.1 | III.64 | 466 | 0.74 min HPLC-G | S: 100° C., overnight |
| 1.106 | 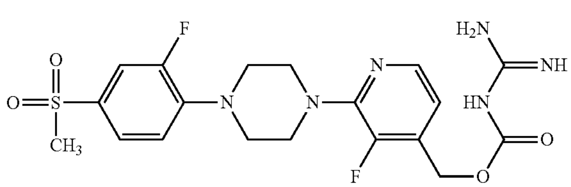 [SMILES: CS(=O)(=O)c1ccc(N2CCN(c3nccc(COC(=O)NC(=N)N)c3F)CC2)c(F)c1] | I.1 | III.72 | 469 | 0.84 min HPLC-C | S: 100° C., overnight |

The invention claimed is:

1. A compound of formula (I)

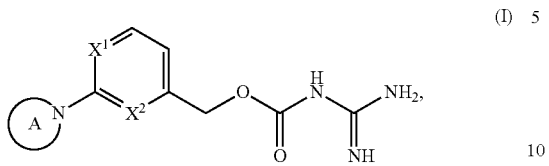

wherein
$X^1$ is selected from the group $X^1$-G1 consisting of: N and CH;
$X^2$ is selected from the group $X^2$-G1 consisting of: N and CF;
with the proviso that at least one of $X^1$ and $X^2$ is N;
A is selected from the group A-G1 consisting of:

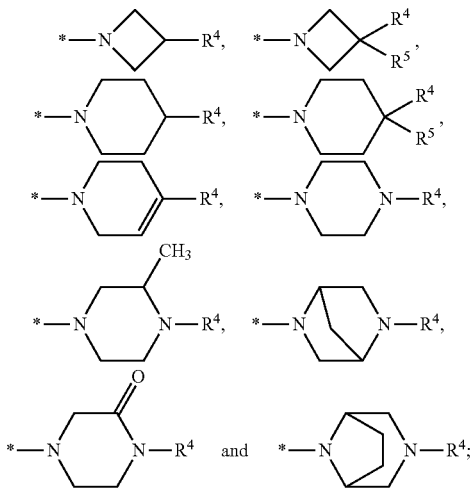

$R^4$ is selected from the group $R^4$-G1 consisting of: azetidinyl, pyrrolidinyl, piperidinyl, piperazinyl, morpholinyl, tetrahydropyranyl, oxazolidinyl, $C_{3-8}$-cycloalkyl, phenyl, pyridinyl, pyrazinyl, pyridazinyl, pyrimidinyl, [1,3,5]triazinyl, triazolyl, thiazolyl, imidazo[1,2-a]pyridin-2-yl, 2,3-dihydro-1H-isoindolyl, oxazolyl and oxadiazolyl,
  wherein each $R^4$ is optionally substituted with one or more groups independently of each other selected from the group consisting of halogen, OH, $CO_2H$, CN, $CF_3$, $C_{1-3}$-alkyl, $C_{3-6}$-cycloalkyl, $C_{1-3}$-alkyl-O—, $(R^N)_2N$—, $C_{1-3}$-alkyl-C(=O)—, $C_{1-4}$-alkyl-O—C(=O)—, $(R^N)_2N$—C(=O)—, $(R^N)_2N$—$C_{1-3}$-alkyl-, $C_{3-6}$-cycloalkyl-$C_{1-3}$-alkyl-O—, $C_{1-3}$-alkyl-$SO_2$—, $(R^N)_2N$—$SO_2$—, 2-oxo-pyrrolidinyl and $C_{1-3}$-alkyl-C(=O)—$(R^N)N$—$C_{1-3}$-alkyl-; and
  wherein a —$CH_2$— group of the pyrrolidinyl, 2,3-dihydro-1H-isoindolyl, oxazolidinyl, piperidinyl or piperazinyl group of $R^4$ is optionally replaced with a —C(=O)—, —S(=O)— or —S(=O)$_2$— group;
$R^N$ is selected from the group $R^4$-G1 consisting of: H and $C_{1-4}$-alkyl, wherein, if several $R^N$ groups are present, they may be identical or different from one another;
$R^5$ is selected from the group $R^5$-G1 consisting of: CN and OH;

or, $R^4$ and $R^5$ groups together with the carbon atom, to which they are attached, may form the following group:

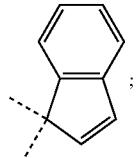

wherein each of the above-mentioned alkyl and —O-alkyl groups may be linear or branched and are optionally substituted by one or more F;
or a pharmaceutically acceptable salt thereof.

2. The compound according to claim 1, wherein A is

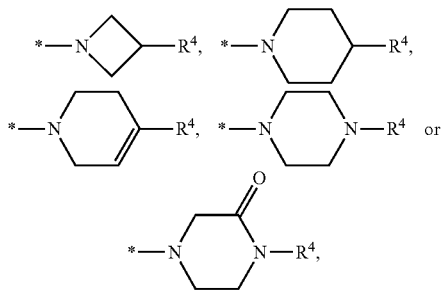

or a pharmaceutically acceptable salt thereof.

3. The compound according to claim 2, wherein A is

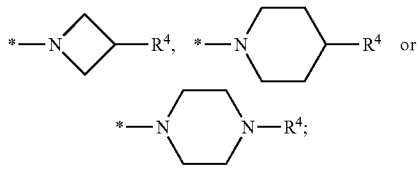

or a pharmaceutically acceptable salt thereof.

4. The compound according to claim 1, wherein $R^4$ is selected from the group consisting of:
  azetidinyl, piperidinyl, piperazinyl, morpholinyl, tetrahydropyranyl, oxazolidinyl, $C_{3-8}$-cycloalkyl, phenyl, pyridinyl, pyridazinyl, pyrimidinyl, [1,3,5]triazinyl, thiazolyl, 2,3-dihydro-1H-isoindolyl and oxazolyl,
    wherein each $R^4$ is optionally substituted with one or more groups independently of each other selected from the group consisting of halogen, $CO_2H$, CN, $CF_3$, $C_{1-3}$-alkyl, $C_{3-6}$-cycloalkyl, $C_{1-3}$-alkyl-O—, $C_{1-3}$-alkyl-C(=O)—, $C_{1-4}$-alkyl-O—C(=O)—, $(R^N)_2N$—C(=O)—, $(R^N)_2N$—$C_{1-3}$-alkyl-, $C_{3-6}$-cycloalkyl-$C_{1-3}$-alkyl-O—, $C_{1-3}$-alkyl-$SO_2$—, $(R^N)_2N$—$SO_2$— and 2-oxo-pyrrolidinyl; and
    wherein a —$CH_2$— group of the 2,3-dihydro-1H-isoindolyl, oxazolidinyl, piperidinyl or piperazinyl group of $R^4$ is optionally replaced with a —C(=O)—, —S(=O)— or —S(=O)$_2$— group;
or a pharmaceutically acceptable salt thereof.

5. The compound according to claim 4, wherein $R^4$ is selected from the group consisting of:
  piperidinyl, tetrahydropyranyl, phenyl, pyridinyl, pyrimidinyl and 2,3-dihydro-1H-isoindolyl, wherein each R⁴ is optionally substituted with one or more groups independently of each other selected from the group consisting of halogen, CN, $C_{1-3}$-alkyl, $C_{1-3}$-alkyl-O—, $C_{1-3}$-alkyl-C(=O)—, $C_{1-4}$-alkyl-O—C(=O)—, $(R^N)_2N$—C(=O)—, $C_{1-3}$-alkyl-SO₂— and $(R^N)_2N$—SO₂—; and wherein a —CH₂— group of the 2,3-dihydro-1H-isoindolyl of R⁴ is optionally replaced with a —C(=O)— group; and $R^N$ is H or CH₃;

or a pharmaceutically acceptable salt thereof.

6. The compound according to claim 1, wherein
X¹ is N and X² is CF;
or a pharmaceutically acceptable salt thereof.

7. The compound according to claim 1, wherein
X¹ is N and X² is CF;
A is selected from the group consisting of:

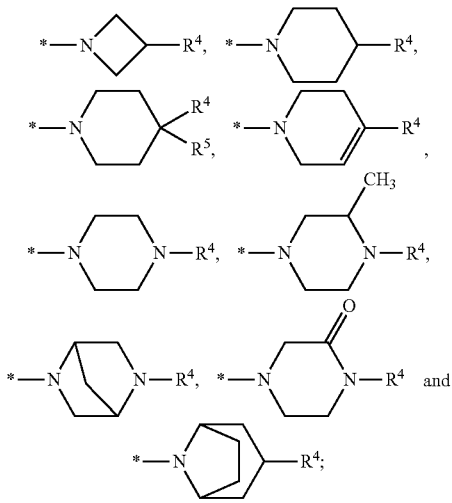

R⁴ is selected from the group consisting of: azetidinyl, piperidinyl, piperazinyl, morpholinyl, tetrahydropyranyl, oxazolidinyl, $C_{3-8}$-cycloalkyl, phenyl, pyridinyl, pyridazinyl, pyrimidinyl, [1,3,5]triazinyl, thiazolyl, 2,3-dihydro-1H-isoindolyl and oxazolyl, wherein each R⁴ is optionally substituted with one or more groups independently of each other selected from the group consisting of halogen, CO₂H, CN, CF₃, $C_{1-3}$-alkyl, $C_{3-6}$-cycloalkyl, $C_{1-3}$-alkyl-O—, $C_{1-3}$-alkyl-C(=O)—, $C_{1-4}$-alkyl-O—C(=O)—, $(R^N)_2N$—C(=O)—, $(R^N)_2N$—$C_{1-3}$-alkyl-, $C_{3-6}$-cycloalkyl-$C_{1-3}$-alkyl-O—, $C_{1-3}$-alkyl-SO₂—$(R^N)_2N$—SO₂— and 2-oxo-pyrrolidinyl; and wherein a —CH₂— group of the 2,3-dihydro-1H-isoindolyl, oxazolidinyl, piperidinyl or piperazinyl group of R⁴ is optionally replaced with a —C(=O)— or —S(=O)— group;

$R^N$ is H or CH₃, wherein, if several $R^N$ groups are present, they may be identical or different from one another; and R⁵ is CN;

or, R⁴ and R⁵ groups together with the carbon atom, to which they are attached, may form the following group:

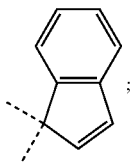

wherein each of the above-mentioned alkyl and —O-alkyl groups may be linear or branched and are optionally substituted by one or more F;

or a pharmaceutically acceptable salt thereof.

8. The compound according to claim 1, wherein
X¹ is N and X² is CF, or
X¹ is CH and X² is N, or
X¹ is N and X² is N;
A is

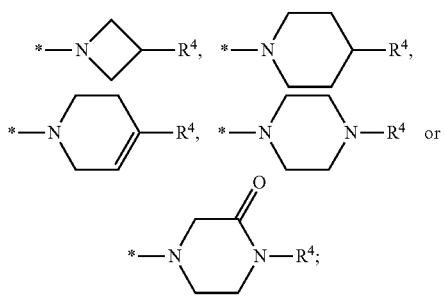

R⁴ is selected from the group consisting of piperidinyl, tetrahydropyranyl, phenyl, pyridinyl, pyrimidinyl and 2,3-dihydro-1H-isoindolyl, wherein each R⁴ is optionally substituted with one substituent selected from the group consisting of F, Cl, CN, CH₃, CF₃, —CH₂CH₃, —CH₂—N(CH₃)₂, —CO₂H, —(C=O)—O—CH₃, —C(=O)—CH₃, —C(=O)—NH₂, —C(=O)—N(CH₃)₂, —SO₂—NH₂ and —SO₂—CH₃;

or wherein R⁴ may be substituted with two substituents, which are independently of each other selected from the group consisting of F, CN and CH₃;

or a pharmaceutically acceptable salt thereof.

9. The compound according to claim 1 selected from:

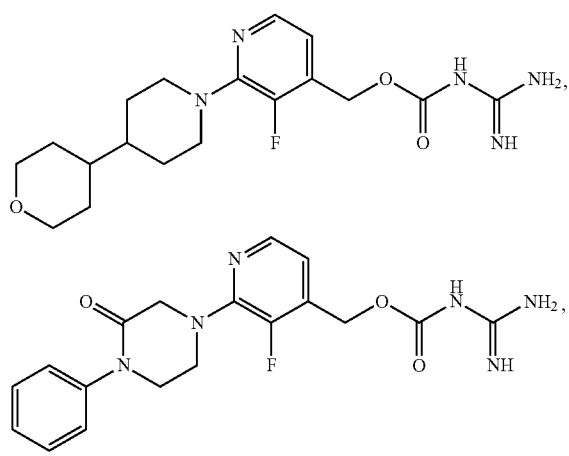

87
-continued
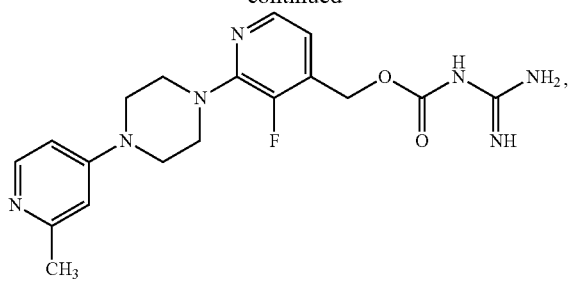
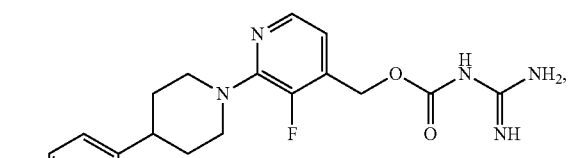
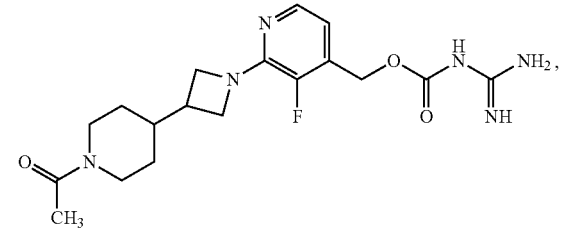
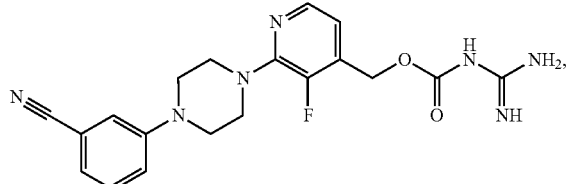
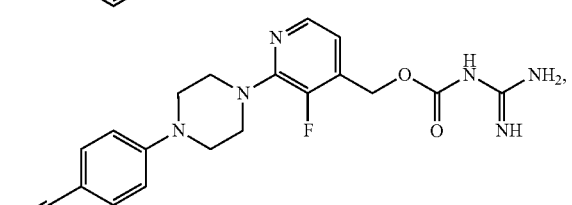
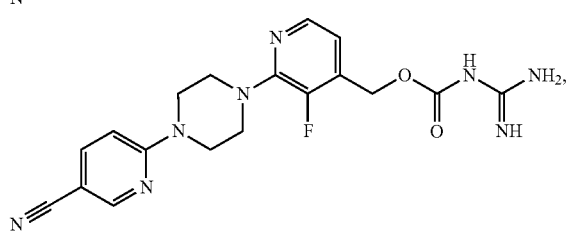
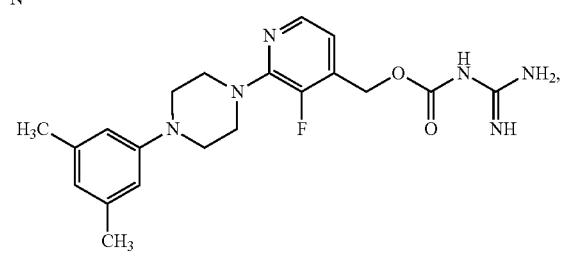
88
-continued
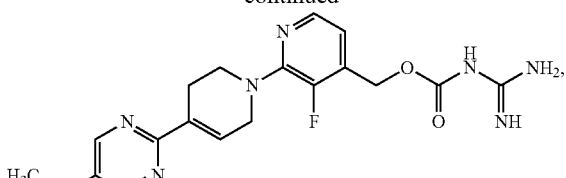
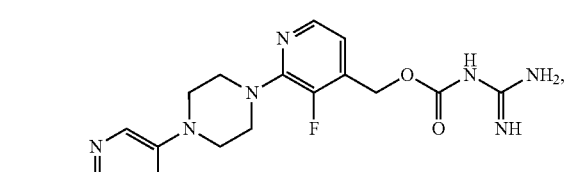
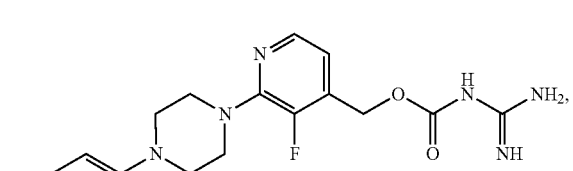
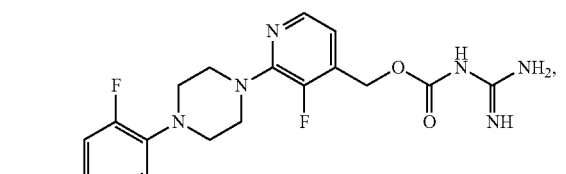
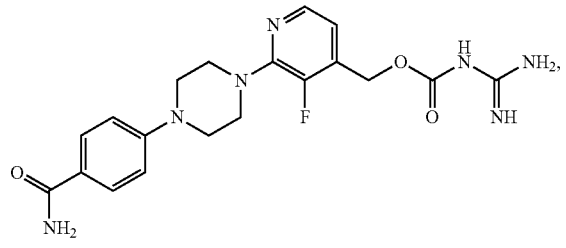
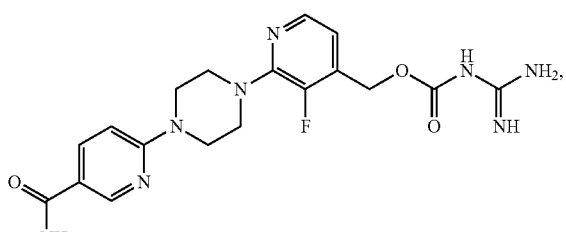
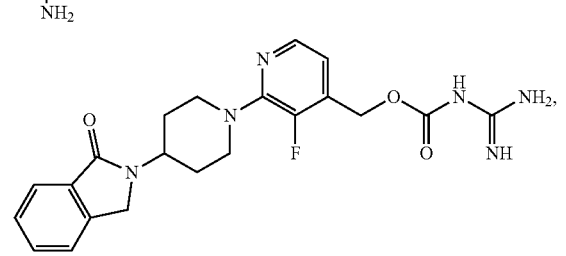

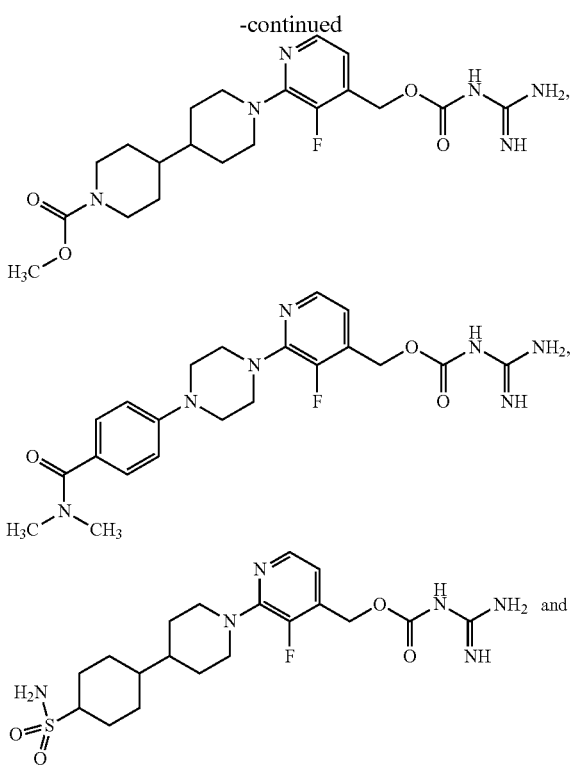

or a pharmaceutically acceptable salt thereof.

10. A pharmaceutically acceptable salt of a compound according to claim 1.

11. A method for therapeutically treating NASH (non-alcoholic steatohepatitis), retinopathy or nephropathy, the method comprising administering a compound according to claim or a pharmaceutically acceptable salt thereof, to a patient in need thereof.

12. A pharmaceutical composition comprising a compound according to claim 1 or a pharmaceutically acceptable salt thereof, optionally together with one or more inert carriers and/or diluents.

13. A pharmaceutical composition comprising one or more compounds according to claim 1 or a pharmaceutically acceptable salt thereof and one or more additional therapeutic agents, optionally together with one or more inert carriers and/or diluents.

* * * * *